(12) United States Patent
Xu et al.

(10) Patent No.: US 11,518,744 B2
(45) Date of Patent: Dec. 6, 2022

(54) BENZAMIDE COMPOUND AND PREPARATION METHOD, USE, AND PHARMACEUTICAL COMPOSITION THEREOF

(71) Applicant: INSTITUTE OF MATERIA MEDICA, CHINESE ACADEMY OF MEDICAL SCIENCES, Beijing (CN)

(72) Inventors: Heng Xu, Beijing (CN); Xiaoguang Chen, Beijing (CN); Songwen Lin, Beijing (CN); Ming Ji, Beijing (CN); Nina Xue, Beijing (CN); Deyu Wu, Beijing (CN); Jing Jin, Beijing (CN)

(73) Assignee: INSTITUTE OF MATERIA MEDICA, CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

(21) Appl. No.: 16/966,433

(22) PCT Filed: Jan. 30, 2019

(86) PCT No.: PCT/CN2019/073942
§ 371 (c)(1),
(2) Date: Oct. 16, 2020

(87) PCT Pub. No.: WO2019/149223
PCT Pub. Date: Aug. 8, 2019

(65) Prior Publication Data
US 2021/0047270 A1 Feb. 18, 2021

(30) Foreign Application Priority Data
Jan. 30, 2018 (CN) .......................... 201810090951.0

(51) Int. Cl.
C07D 213/53 (2006.01)
C07D 401/12 (2006.01)
C07D 405/12 (2006.01)
C07D 409/12 (2006.01)

(52) U.S. Cl.
CPC ......... *C07D 213/53* (2013.01); *C07D 401/12* (2013.01); *C07D 405/12* (2013.01); *C07D 409/12* (2013.01)

(58) Field of Classification Search
CPC ..................................... C07D 213/53
USPC ........................................ 546/255
See application file for complete search history.

(56) References Cited

U.S. PATENT DOCUMENTS 5,962,682 A  10/1999  Breu et al.
10,112,948 B2  10/2018  Debrabander et al.

FOREIGN PATENT DOCUMENTS

| CN | 1944398 A | 4/2007 |
|---|---|---|
| CN | 107949279 A | 4/2018 |
| WO | 96/40100 A1 | 12/1996 |
| WO | 9640100 A1 | 12/1996 |
| WO | 2005/085188 A2 | 9/2005 |
| WO | 2010/023448 A1 | 3/2010 |
| WO | 2017/007634 A1 | 1/2017 |

OTHER PUBLICATIONS

Extended European Search Report for European Patent Application No. 19747114.7 dated May 3, 2021, 7 pages.
International Search Report and Written Opinion from International Application No. PCT/CN2019/073942, dated Apr. 30, 2019.
Japanese Office Action for JP Application No. 2020-541673 dated Oct. 26, 2021 (10 pages, with English translation).
Registry(STN) [online], Apr. 20, 2007, [search date] Sep. 6, 2021CAS Registration No. 931303 to 98-9.
Registry(STN) [online], Jan. 29, 2009, [search date] Sep. 6, 2021CAS Registration No. 1097508 to 92-3.
Registry(STN) [online], May 27, 2011, [search date] Sep. 6, 2021CAS Registration No. 1301538 to 19-1.
Registry(STN) [online], Apr. 9, 2008, [search date] Sep. 6, 2021CAS Registration No. 1013247 to 59-0.
Registry(STN) [online], Jun. 27, 2008, [search date] Sep. 6, 2021CAS Registration No. 1031176 to 50-7.
Registry(STN) [online], May 25, 2011, [search date] Sep. 6, 2021CAS Registration No. 1300268 to [03]-[4].
Registry(STN) [online], Jan. 10, 2006, [search date] Sep. 6, 2021CAS Registration No. 871545 to 23-2.
Registry(STN) [online], Apr. 3, 2007, [search date] Sep. 6, 2021CAS Registration No. 928917 to 55-9.
Registry(STN) [online], Apr. 3, 2007, [search date] Sep. 6, 2021CAS Registration No. 929000 to 21-5.
Registry(STN) [online], Apr. 20, 2007, [search date] Sep. 6, 2021CAS Registration No. 931236 to 91-8.
Registry(STN) [online], Jun. 27, 2008, [search date] Sep. 6, 2021CAS Registration No. 1031142 to 21-8.

(Continued)

*Primary Examiner* — Taofiq A Solola
(74) *Attorney, Agent, or Firm* — Merchant & Gould P.C.

(57) ABSTRACT

The present invention relates to a benzamide compound and a preparation method, use and pharmaceutical composition thereof. The benzamide compound represented by formula (I) is a STAT3 inhibitor, and can be used to prevent and/or treat a disease related to STAT3 activity, such as a tumor, autoimmune disease, renal disease, cardiovascular disease, inflammation, metabolic/endocrine dysfunction, and neurological disease.

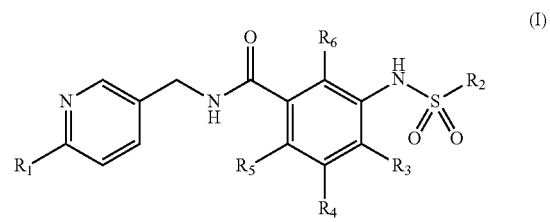

(I)

10 Claims, 2 Drawing Sheets

(56) References Cited

OTHER PUBLICATIONS

Registry(STN) [online], Dec. 12, 2008, [search date] Sep. 6, 2021CAS Registration No. 1083341 to 86-9.
Registry(STN) [online], Apr. 7, 2011, [search date] Sep. 6, 2021CAS Registration No. 1276379 to 19-1.
Registry(STN) [online], May 12, 2011, [search date] Sep. 6, 2021CAS Registration No. 1293790 to 34-7.
Registry(STN) [online], May 22, 2011, [search date] Sep. 6, 2021CAS Registration No. 1298349 to 21-9.
Registry(STN) [online], Aug. 6, 2012, [search date] Sep. 6, 2021CAS Registration No. 1386814 to 57-8.
Registry(STN) [online], Jul. 8, 2015, [search date] Sep. 6, 2021CAS Registration No. 1797346 to 76-9.

BENZAMIDE COMPOUND AND PREPARATION METHOD, USE, AND PHARMACEUTICAL COMPOSITION THEREOF

This application is a National Stage Application of PCT/CN2019/073942, filed Jan. 30, 2019, which claims benefit of Chinese Patent Application No. 201810090951.0, filed Jan. 30, 2018, which applications are incorporated herein by reference. To the extent appropriate, a claim of priority is made to each of the above-disclosed applications.

TECHNICAL FIELD

This invention relates to the technical field of pharmacy, and relates to a type of benzamide compounds, a preparation method, use, and a pharmaceutical composition thereof.

BACKGROUND ART

The Signal Transducer and Activator of Transcription (STAT) protein family performs dual functions of signal transduction and transcription regulation. Although the members of the STAT family are similar in structure, they are involved in different cellular processes. There are currently 7 STAT-family members that have been isolated and purified, namely STAT1, STAT2, STAT3, STAT4, STAT5A, STAT5B and STAT6.

As a member of the STAT family, STAT3 plays an important role in the occurrence and development of cancer, inflammation, ischemia/reperfusion injury, and self-renewal of stem cell. STAT3 can be activated by receptor tyrosine kinases and non-receptor tyrosine kinases. When cytokine binds to its receptor, dimerization of the receptor occurs and leads to phosphorylation of JAK kinase, thus making phosphorylation of the tyrosine residue (Tyr705) at the C-terminal of the STAT3 molecule, and therefore the STAT3 molecule is activated through the formation of dimer in its SH2 region and transferred into the nucleus to bind to specific DNA sequences and regulate the transcription of target genes. In addition, Ser727 located in the Stat3 transcription activation domain is further activated by the MAPK or mTOR pathway to regulate Stat3 transcription activity, and this is considered to be necessary for its complete activation. In addition to the phosphorylation of Tyr705 and Ser727, acetylation of Lys685 stabilizes the Stat3 dimer and regulates the Stat3 activity.

At present, some STAT3 inhibitors have entered the clinical research stage for the treatment of tumor and autoimmune diseases. The STAT3 inhibitor napabucasin developed by Boston Biomedical Co., Ltd. was approved the FDA orphan drug designation in June 2016 for the treatment of gastroesophageal junction cancer, and it is currently in the phase III clinical trial stage; while the STAT3 inhibitor napabucasin was approved the FDA orphan drug designation in November 2016 for the treatment of pancreatic cancer and is currently in the phase III clinical trial stage. There are also some STAT3 inhibitors in various clinical trials. For example, the STAT3 inhibitor GLG-302 developed by GLG is in the phase I clinical trials for the treatment of tumors and polycystic kidney disease; and GLG-801 used for the treatment of kidney disease, Leukemia and psoriasis is in the phase II clinical trials. The STAT3 inhibitor MOL-4249 developed by Moleculin Biotechnology is used for the treatment of mild to moderate psoriasis and is currently in the phase II clinical trial. Takeda's AK-114 is used for treating ulcerative colitis and is currently in phase II clinical research stage.

STAT3 has become a very attractive drug target. However, there is still a need to develop safer and more effective STAT3 inhibitors for prevention and/or treatment of tumors, autoimmune diseases, renal diseases, cardiovascular diseases, inflammation, metabolic/endocrine dysfunction or neurological diseases.

Content of Invention

The technical problem solved by the present invention is to provide a new STAT3 inhibitor, a preparation method, a pharmaceutical composition and use thereof. The STAT3 inhibitor has strong inhibitory activity on tumor cells with high expression of STAT, especially on human prostate cancer cell DU-145, thus having better prevention and/or treatment effects on diseases mediated by STAT3, such as tumors, autoimmune diseases, renal diseases, cardiovascular diseases, inflammation, metabolic/endocrine dysfunction or neurological diseases.

In order to solve the above technical problem, the present invention provides the following technical solutions.

The first aspect of the present invention is to provide a compound represented by Formula (I), or a stereoisomer, a geometric isomer, a tautomer or a pharmaceutically acceptable salt thereof:

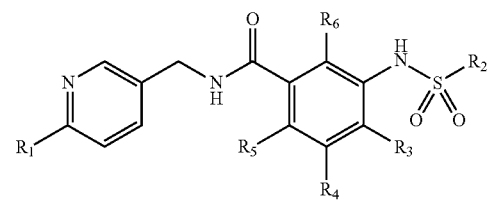

wherein $R_1$ is selected from hydrogen, cyano, difluoromethyl, trifluoromethyl, halogen, $C_{1-3}$ alkyl, $C_{1-3}$ alkoxy;

$R_2$ is selected from 6- to 10-membered aryl or 5- to 10-membered heteroaryl; wherein the 6- to 10-membered aryl or 5- to 10-membered heteroaryl is optionally substituted by m Ra; or the 6- to 10-membered aryl or 5- to 10-membered heteroaryl is 6- to 10-membered aryl fused to 4- to 6-membered cycloalkene or 4- to 6-membered heterocycloalkene or 5- to 10-membered heteroaryl fused to 4- to 6-membered cycloalkene or 4- to 6-membered heterocycloalkene;

each Ra is independently selected from the following groups: cyano, difluoromethyl, trifluoromethyl, halogen, $C_{1-3}$ alkyl, $C_{3-7}$ cycloalkyl, $C_{1-3}$ alkoxy;

m is 0, 1, 2, 3, 4 or 5;

$R_3$, $R_4$, $R_5$ and $R_6$ are each independently selected from hydrogen, cyano, difluoromethyl, trifluoromethyl, halogen, $C_{1-3}$ alkyl, $C_{1-3}$ alkoxy.

In a further preferred embodiment, $R_1$ is selected from hydrogen, cyano, difluoromethyl, trifluoromethyl, chlorine, methyl, ethyl, n-propyl, isopropyl, methoxy or ethoxy.

In another preferred embodiment, the present invention provides a compound represented by Formula (I), or a stereoisomer, a geometric isomer, a tautomer or a pharmaceutically acceptable salt thereof:

wherein

R₁ is selected from hydrogen, cyano, difluoromethyl, trifluoromethyl, halogen, $C_{1-3}$ alkyl, $C_{1-3}$ alkoxy; preferably selected from hydrogen, cyano, difluoromethyl, trifluoromethyl, chlorine, methyl, ethyl, n-propyl, isopropyl, methoxy or ethoxy.

R₂ is selected from:

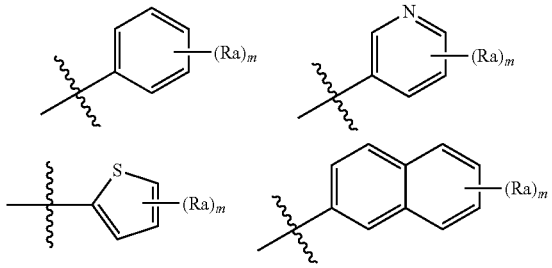

each Ra is independently selected from the following groups: cyano, difluoromethyl, trifluoromethyl, halogen, $C_{1-3}$ alkyl, $C_{3-7}$ cycloalkyl, $C_{1-3}$ alkoxy;

m is 0, 1, 2, 3, 4 or 5;

R₃, R₄, R₅ and R₆ are each independently selected from hydrogen, cyano, difluoromethyl, trifluoromethyl, halogen, $C_{1-3}$ alkyl, $C_{1-3}$ alkoxy.

In a further preferred embodiment, R₂ is selected from:

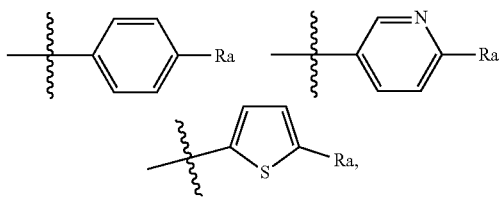

Ra is selected from the following groups: cyano, difluoromethyl, trifluoromethyl, halogen, $C_{1-3}$ alkyl, $C_{3-7}$ cycloalkyl or $C_{1-3}$ alkoxy.

In a further preferred embodiment, Ra is selected from the following groups: chlorine, methyl, ethyl, cyclopropyl, methoxy or ethoxy.

In another preferred embodiment, the present invention provides a compound represented by Formula (I), or a stereoisomer, a geometric isomer, a tautomer or a pharmaceutically acceptable salt thereof:

wherein

R₁ is selected from hydrogen, cyano, difluoromethyl, trifluoromethyl, halogen, $C_{1-3}$ alkyl, $C_{1-3}$ alkoxy; preferably selected from hydrogen, cyano, difluoromethyl, trifluoromethyl, chlorine, methyl, ethyl, n-propyl, isopropyl, methoxy or ethoxy.

R₂ is selected from:

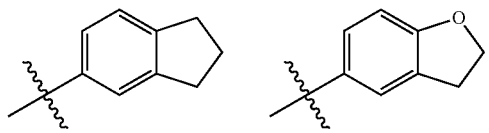

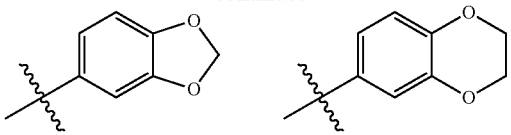

R₃, R₄, R₅, R₆ are each independently selected from hydrogen, cyano, difluoromethyl, trifluoromethyl, halogen, $C_{1-3}$ alkyl, $C_{1-3}$ alkoxy.

In a still further preferred embodiment, the present invention provides a compound represented by Formula (I), or a stereoisomer, a geometric isomer, a tautomer or a pharmaceutically acceptable salt thereof:

wherein

R₁ is selected from hydrogen, cyano, difluoromethyl, trifluoromethyl, halogen, $C_{1-3}$ alkyl, $C_{1-3}$ alkoxy; preferably selected from hydrogen, cyano, difluoromethyl, trifluoromethyl, chlorine, methyl, ethyl, n-propyl, isopropyl, methoxy or ethoxy.

R₂ is selected from 6- to 10-membered aryl or 5- to 10-membered heteroaryl; wherein, the 6- to 10-membered aryl or 5- to 10-membered heteroaryl is optionally substituted by m Ra;

each Ra is independently selected from the following groups: cyano, difluoromethyl, trifluoromethyl, halogen, $C_{1-3}$ alkyl, $C_{3-7}$ cycloalkyl, $C_{1-3}$ alkoxy;

m is 0, 1, 2, 3, 4 or 5;

preferably, R₂ is selected from:

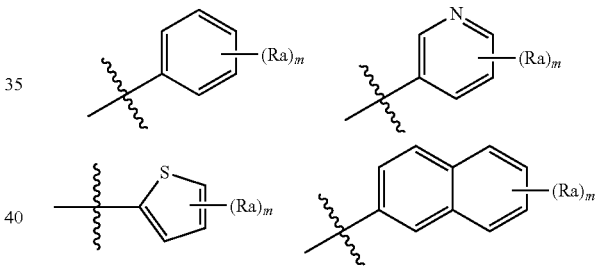

each Ra is independently selected from cyano, difluoromethyl, trifluoromethyl, halogen, $C_{1-3}$ alkyl, $C_{3-7}$ cycloalkyl, $C_{1-3}$ alkoxy;

m is 0, 1, 2, 3, 4 or 5;

more preferably, R₂ is selected from:

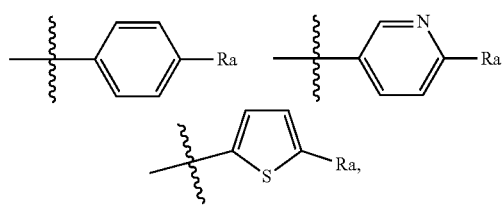

Ra is selected from the following groups: cyano, difluoromethyl, trifluoromethyl, halogen, $C_{1-3}$ alkyl, $C_{3-7}$ cycloalkyl or $C_{1-3}$ alkoxy;

further preferably, Ra is selected from the following groups: chlorine, methyl, ethyl, cyclopropyl, methoxy or ethoxy;

or R₂ is selected from 6- to 10-membered aryl or 5- to 10-membered heteroaryl; wherein, the 6- to 10-membered aryl or 5- to 10-membered heteroaryl is 6- to 10-membered aryl fused to 4- to 6-membered cycloalkene or 4- to 6-membered heterocycloalkene or 5- to 10-membered heteroaryl fused to 4- to 6-membered cycloalkene or 4- to 6-membered heterocycloalkene;

preferably, $R_2$ is selected from:

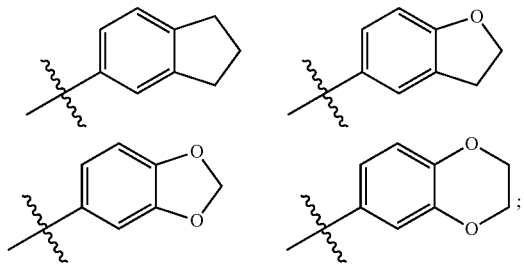

$R_3$, $R_4$, $R_5$, $R_6$ are each independently selected from hydrogen, cyano, difluoromethyl, trifluoromethyl, fluorine, chlorine, methyl, ethyl, methoxy.

In a further preferred embodiment, $R_3$ is selected from methyl, and $R_4$, $R_5$ and $R_6$ are all selected from hydrogen.

Specifically, the preferred compounds according to the present invention are as follows:

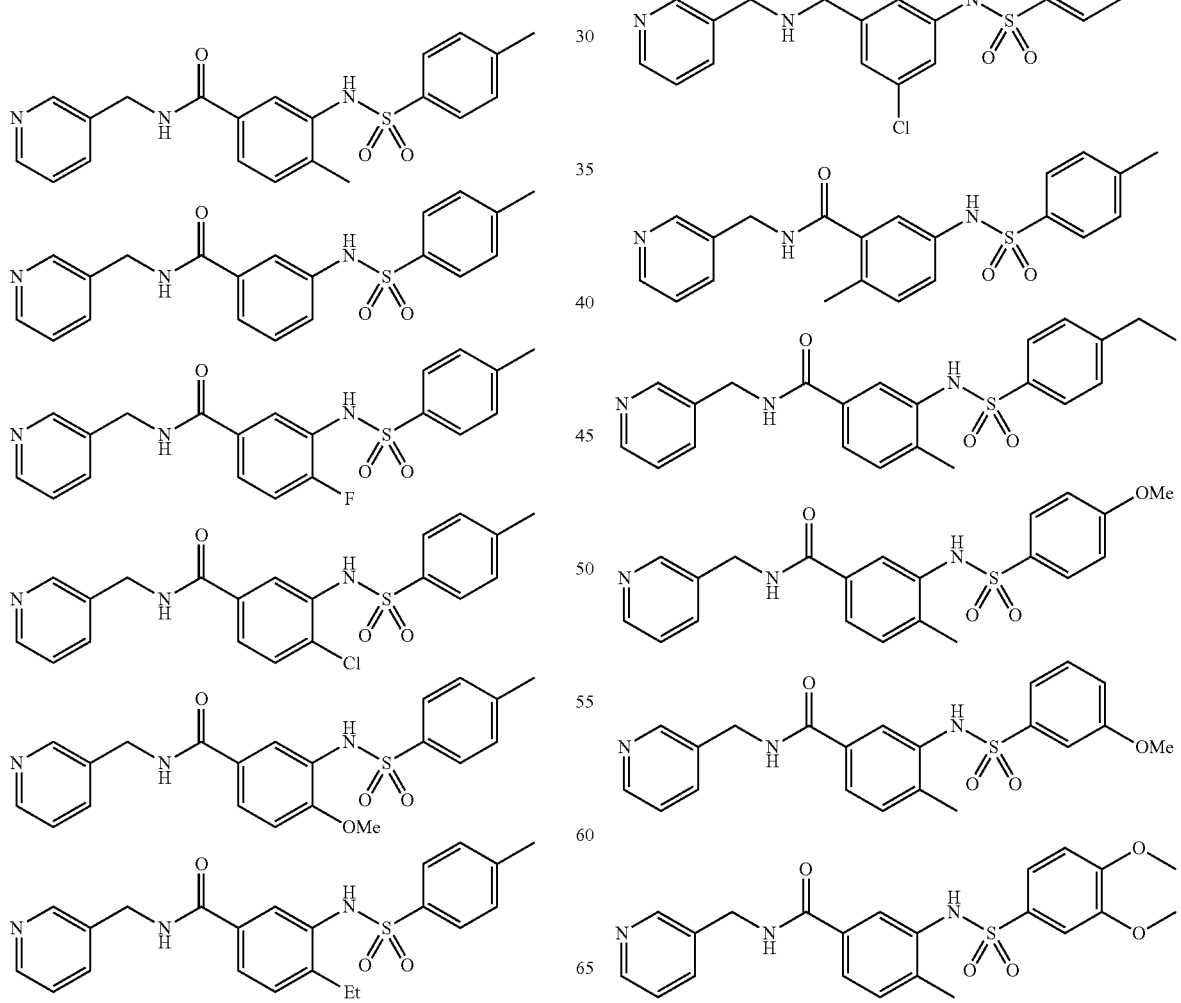

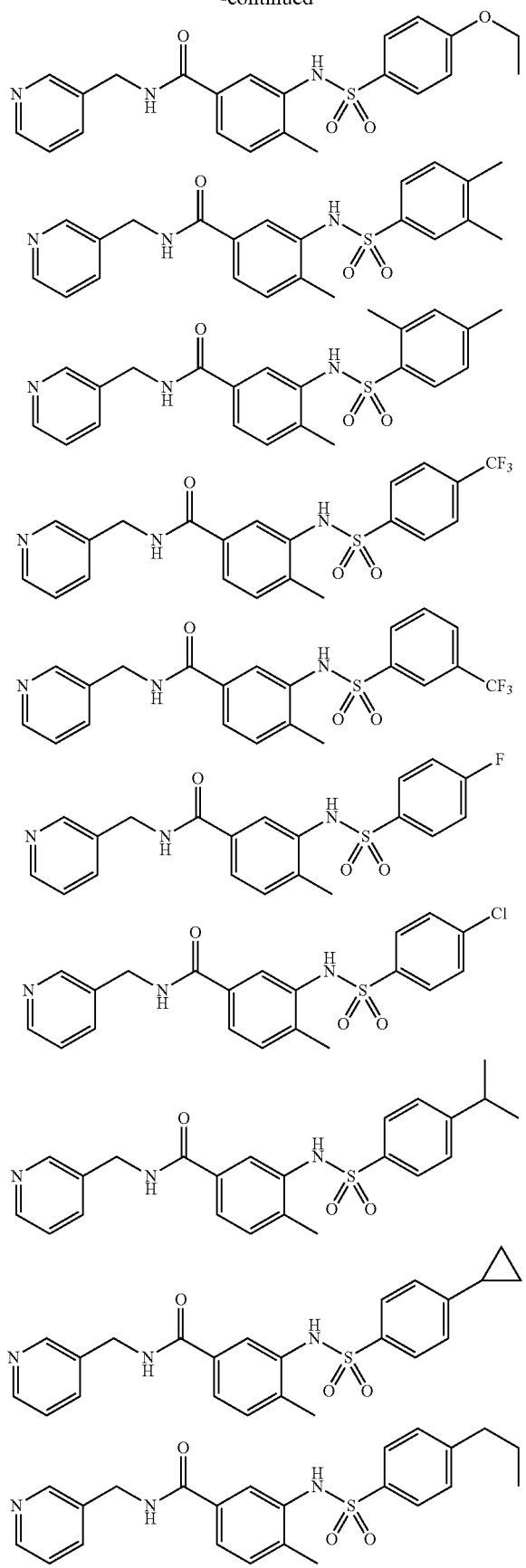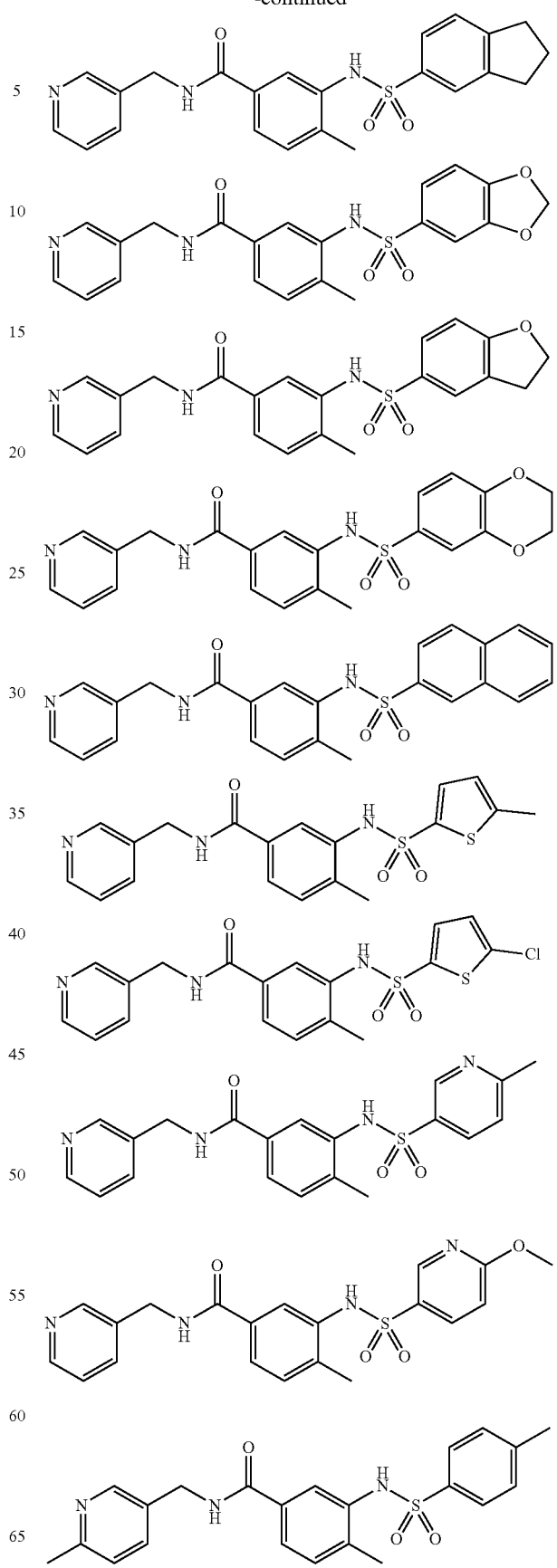

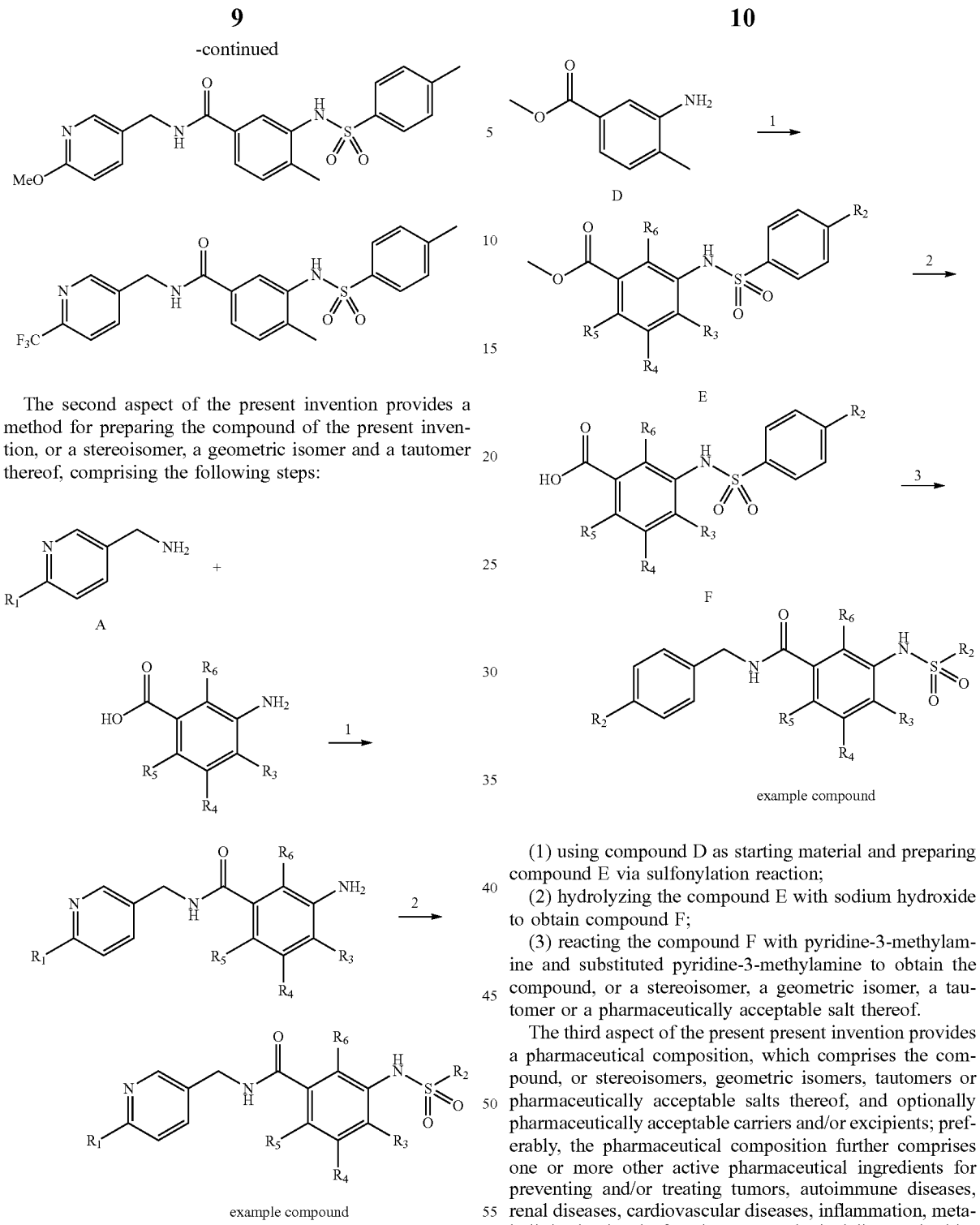

The second aspect of the present invention provides a method for preparing the compound of the present invention, or a stereoisomer, a geometric isomer and a tautomer thereof, comprising the following steps:

(1) using compounds A and B as starting materials and preparing compound C via condensation reaction;

(2) reacting the compound C via sulfonylation reaction to obtain the compound, or a stereoisomer, a geometric isomer, a tautomer or a pharmaceutically acceptable salt thereof.

The second aspect of the present invention also provides another method for preparing the compound, or a stereoisomer, a geometric isomer and a tautomer thereof, comprising the following steps:

(1) using compound D as starting material and preparing compound E via sulfonylation reaction;

(2) hydrolyzing the compound E with sodium hydroxide to obtain compound F;

(3) reacting the compound F with pyridine-3-methylamine and substituted pyridine-3-methylamine to obtain the compound, or a stereoisomer, a geometric isomer, a tautomer or a pharmaceutically acceptable salt thereof.

The third aspect of the present present invention provides a pharmaceutical composition, which comprises the compound, or stereoisomers, geometric isomers, tautomers or pharmaceutically acceptable salts thereof, and optionally pharmaceutically acceptable carriers and/or excipients; preferably, the pharmaceutical composition further comprises one or more other active pharmaceutical ingredients for preventing and/or treating tumors, autoimmune diseases, renal diseases, cardiovascular diseases, inflammation, metabolic/endocrine dysfunction or neurological diseases besides the compound, or stereoisomers, geometric isomers, tautomers or pharmaceutically acceptable salts thereof; preferably, the pharmaceutical composition is a pharmaceutically acceptable pharmaceutical preparation for preventing and/or treating tumors, autoimmune diseases, renal diseases, cardiovascular diseases, inflammation, metabolic/endocrine dysfunction or neurological diseases.

In another aspect, the present invention also provides a pharmaceutical preparation, which comprises at least one compound mentioned above, or a stereoisomer, a geometric isomer, a tautomer or a pharmaceutically acceptable salt thereof, and optionally a pharmaceutically acceptable carrier and/or excipient. Preferably, the pharmaceutical preparation is selected from the following preparations: parenteral preparation, such as solution for injection or suspension; enteral preparation, such as oral preparation, e.g. tablet or capsule; topical preparation such as lotion, gel, ointment, emulsion, nasal preparation, suppository, transdermal preparation or ophthalmic preparation.

In another aspect, the present invention also provides use of the compound, or a stereoisomer, a geometric isomer, a tautomer or a pharmaceutically acceptable salt thereof, or the pharmaceutical composition in the preparation of a medicament for preventing and/or treating tumors, immune diseases, renal diseases, cardiovascular diseases, inflammation, metabolism/endocrine dysfunction or neurological diseases. In other words, the present invention provides a method for prevention and/or treatment of tumors, immune diseases, renal diseases, cardiovascular diseases, inflammation, metabolism/endocrine dysfunction or neurological diseases. The method comprises administering a prophylactically and/or therapeutically effective amount of the compound, the stereoisomer, the geometric isomer, the tautomer or the pharmaceutically acceptable salt thereof, or the pharmaceutical composition to a subject in need.

Some of the terms used in the present invention are defined as follows, and other undefined terms have the meaning known to those skilled in the art.

Halogen refers to fluorine, chlorine, bromine or iodine.

$C_{1-3}$ alkyl refers to a straight or branched saturated aliphatic hydrocarbon group having 1 to 3 carbon atoms. Examples of such groups include, but are not limited to: methyl, ethyl, propyl, isopropyl.

$C_{1-3}$ alkoxy refers to —O-alkyl, wherein the alkyl contains 1 to 3 carbon atoms and is straight, branched or cyclic. Examples of such groups include, to but are not limited to: methoxy, ethoxy, n-propoxy, iso-propoxy, or cyclopropoxy.

$C_{3-7}$ cycloalkyl refers to a saturated monocyclic, fused, spiral or polycyclic structure having 3 to 7 carbon ring atoms. Examples of such groups include, but are not limited to: cyclopropyl, cyclobutyl, cyclopentyl, cyclopentenyl, cyclohexyl and cycloheptyl.

$C_{4-6}$ cycloalkene refers to a monocyclic structure with 4 to 6 carbon ring atoms and a C=C double bond. Examples of such groups include, but are not limited to, cyclobutene, cyclopentene and cyclohexene.

$C_{4-6}$ heterocycloalkene refers to a monocyclic structure with 4 to 6 ring atoms and a C=C double bond, in which one or more ring atoms are heteroatoms selected from nitrogen, oxygen or S(O)m (wherein m is an integer from 0 to 2) but ring parts of —O—O—, —O—S— or —S—S— are not included, and the rest ring atoms are carbon atoms. Examples of such groups include but not limited to 2,3-dihydrofuran, 2,5-dihydrofuran, 1,3-m-dioxacyclopentene, 1,4-dioxa-2-hexene, 2,3-dihydro-1H-pyrrole, 1,2,3,4-tetrahydropyridine, 1,2,3,6-tetrahydropyridine.

$C_{1-3}$ alkylamino refers to —NHR, wherein R is $C_{1-3}$ alkyl, and examples of such groups include but not limited to methylamino, ethylamino, propylamino, isopropylamino or cyclopropylamino.

Di ($C_{1-3}$ alkyl) amino refers to —NR'R, wherein R' and R are independently $C_{1-3}$ alkyl. Examples of such groups include but not limited to dimethylamino, diethylamino, dipropylamino, diisopropylamino, methylethylamino, methylpropylamino, methylisopropylamino, ethylpropylamino, ethylisopropylamino and propylisopropylamino.

Aryl refers to a monocyclic or bicyclic aromatic carbocyclic group, which usually has 6-10 carbon atoms; such as phenyl or naphthyl; phenyl is preferred.

Heteroaryl refers to 5-10-membered aromatic heterocyclic group, including but not limited to: 5-membered heteroaryl: furyl, thienyl, pyrrolyl, oxazolyl, isoxazolyl, thiazolyl, isothiazolyl, imidazolyl, pyrazolyl, triazolyl (1,2,4-triazolyl, 1,3,4-triazolyl or 1,2,3-triazolyl), thiadiazolyl (1,3,4-thiadiazolyl, 1,2,5-thiadiazolyl, 1,2,3-thiadiazolyl or 1,2,4-thiadiazolyl) and oxadiazolyl (1,3,4-oxadiazolyl, 1,2,5-oxadiazolyl, 1,2,3-oxadiazolyl or 1,2,4-oxadiazolyl); and 6-membered heteroaryl: pyridyl, pyrimidinyl, pyrazinyl and pyridazinyl; and bicyclic groups such as benzofuranyl, benzothiophenyl, indazolyl, purinyl, quinolinyl, isoquinolinyl, phthalazinyl, naphthyridinyl, chinocalinyl, quinazolinyl, cinnolinyl, pteridinyl, indolizinyl, indolyl and isoindolyl. Preferred heteroaryl groups are thienyl, thiazolyl, pyridyl and pyrimidinyl.

"optionally" means that the event or environment described later can but does not necessarily occur, and the description includes the occasion when the event or environment occurs or does not occur. For example, "alkyl optionally substituted by halogen" means that halogen can but does not necessarily exist, and this description includes the case in which alkyl is substituted by halogen and the case in which alkyl is not substituted by halogen.

Compounds of the present invention may contain one or more chiral centers, which exist in different stereoisomeric forms. All stereoisomeric forms of the compounds of the present invention, including but not limited to diastereoisomers, enantiomers and atropisomers, and their mixtures (such as racemic mixtures) are within the scope of the present invention.

The compounds described in the present invention include geometric isomers thereof. For example, if the compounds of the present invention contain double bonds or fused rings, the compounds may have geometric isomers, and their cis-forms, trans-forms and mixtures of cis-forms and trans-forms are all included in the scope of the present invention.

The compounds described in the present invention include tautomers. The tautomers refer to the structural isomers with different energies which are mutually transformed via low energy barriers, such as keto-enol and imine-enamine tautomerization.

The compound of the present invention also includes its isotopically labelled compound, wherein one or more atoms are replaced by an atom having the same atomic number but different atomic mass or mass number found in nature. Examples include but not limited to: hydrogen isotopes $^2$H and $^3$H; carbon isotopes $^{11}$C, $^{13}$C and $^{14}$C; chlorine isotope $^{36}$Cl; fluorine isotope $^{18}$F; iodine isotopes $^{123}$I and $^{125}$I; nitrogen isotopes $^{13}$N and $^{15}$N; oxygen isotopes $^{15}$O, $^{17}$O and $^{18}$O; phosphorus isotope $^{32}$P and sulfur isotope $^{35}$S.

Various hydrates, solvates and polymorphisms of the compound of the present invention or its salt are also included in the scope of the present invention.

The prodrug of the compound of the present invention is also included in the scope of the present invention. Some derivatives of the compound of the present invention have weak or no pharmacological activity themselves, but when these derivatives are administered in vivo or on the body, they can be converted into the compound of the present invention having pharmacological activity by means of such as hydrolytic cleavage, and these derivatives are referred to as prodrugs. Further information on prodrug use can be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

The compound of the present invention includes pharmaceutically acceptable salt. Pharmaceutically acceptable salt refers to a salt that is pharmaceutically acceptable and has pharmacological activity required by the parent compound. The pharmaceutically acceptable salt was described in detail by Berge et al. in J. Pharma. Sci., 1977, 66, 1-19, and the literature is hereby incorporated by reference. The compound of the present invention can include sufficient acidic groups, sufficient alkaline groups or functional groups with both acidic and alkaline properties, and react with corresponding inorganic or organic bases, or inorganic and organic acids to form pharmaceutically acceptable salt. Examples of pharmaceutically acceptable salt include sulfate salt, pyrosulfate salt, bisulfate salt, sulfite salt, bisulfite salt, phosphate salt, monohydrogen phosphate salt, dihydrogen phosphate salt, metaphosphate salt, pyrophosphate salt, hydrochloride salt, hydrobromide salt, hydriodate salt, acetate salt, propionate salt, decanoate salt, caprylate salt, acrylate salt, formate salt, isobutyrate salt, caproate salt, heptylate salt, propiolate salt, oxalate salt, malonate salt, succinate salt, suberate salt, sebacate salt, fumarate salt, maleate salt, butyne-1,4-dicarboxylate salt, hexyne-1,6-dicarboxylate salt, benzoate salt, chlorinated benzoate salt, methylbenzoate salt, dinitrobenzoate salt, hydroxybenzoate salt, methoxybenzoate salt, phthalate salt, sulfonate salt, xylenesulfonate salt, phenylacetate salt, phenylpropionate salt, phenylbutyrate salt, citrate salt, lactate salt, gamma-hydroxybutyrate salt, hydroxyacetate salt, tartrate salt, methane sulfonate salt, propanesulfonate salt, naphthalene-1-sulfonate salt, naphthalene-2-sulfonate salt and mandelate salt.

When the compound of the present invention is used as drug, it is usually administered in the form of pharmaceutical composition. Therefore, pharmaceutical composition comprising the compound of the present invention and pharmaceutically acceptable carriers, diluents or excipients is also included in the scope of the present invention. The carriers, auxiliaries and excipients used herein include any and all solvents, diluents or other liquid excipients, dispersants or suspending agents, surfactants, isotonic agents, thickeners or emulsifiers, preservatives, solid binders, lubricants, etc. suitable for the desired specific preparation. Various carriers for preparing pharmaceutically acceptable compositions and known technique for their preparation are disclosed in Remington: The Science and Practice of Pharmacy, 21$^{st}$ edition, 2005, ed. D. B. Troy, Lippincott Williams&Wilkins, Philadelphia, and Encyclopedia of Pharmaceutical Technology, eds. J. Swarbrick, and J. C. Boylan, 1988-1999, Marcel Dekker, New York, the contents of which are hereby incorporated by reference.

The composition of the present invention can be administered in any route suitable for diseases to be treated, in particular administration routes as follows: parenterally, such as in injection solution or suspension form; transenterally, such as orally, for example in tablet or capsule form; topically, such as in lotion, gel, ointment or emulsion form or in nasal or suppository form. Topical administration is for example applied to the skin. Another form of topical administration is administration to eye.

Pharmaceutical composition can be administered in solid, semi-solid, liquid or gaseous form, or can be as dried powder, such as in freeze-drying form. Pharmaceutical composition can be packaged in transportable form, including, for example, solid preparation such as capsule, medicine capsule, cachet, gelatin, paper, tablet, suppository, pellet, pill, lozenge and pastille. The packaging type generally depends on administration route. Implantable sustained release preparations as well as transdermal preparations are also included.

Examples of materials as pharmaceutically acceptable carrier include, but are not limited to: ion exchanger, alumina, aluminum stearate, lecithin, serum protein (e.g. human serum albumin), buffering substance (e.g., phosphate salt), glycine, sorbic acid and potassium sorbate, partial glyceride mixture of saturated vegetable fatty acids, water, salt or electrolyte (for example, protamine sulfate, disodium hydrogen phosphate, potassium hydrogen phosphate, sodium chloride, zinc salt), colloidal silicon dioxide, magnesium trisilicate, polyvinylpyrrolidone, polyacrylate, wax, polyethylene-polyoxypropylene block copolymer, lanolin, sugar (e.g. lactose, glucose and sucrose), starch (such as corn starch and potato starch), cellulose and its derivatives such as sodium carboxymethyl cellulose, ethyl cellulose and cellulose acetate; tragacanth powder; malt; gelatin; talc powder; excipient such as cocoa butter and wax for suppository; oil such as peanut oil, cottonseed oil, safflower oil, sesame oil, olive oil, corn oil and soybean oil; glycol such as propylene glycol or polyethylene glycol; ester such as ethyl oleate and ethyl laurate; agar; buffer agent such as magnesium hydroxide and aluminum hydroxide; alginic acid; pyrogen-free water; isotonic brine; Ringer's liquid; ethanol; and phosphate buffer, and other non-toxic and compatible lubricants such as sodium lauryl sulfate and magnesium stearate. According to the judge of the personnel for preparing preparation, colorant, releaser, coating agent, sweetener, flavoring agent, fragrant agent, preservative and antioxidant can also be present in the composition.

The compound of the present invention can be used alone or in combination with other therapeutic agents for treating the diseases or conditions (such as cancer) described in the present invention. In some embodiments, the compound of the present invention is combined in pharmaceutical combination preparation or combined in administration scheme as combination therapy with a second compound having high-proliferation resistance or for treating highly proliferative diseases (such as cancer). The second compound in the pharmaceutical combination preparation or quantitative administration scheme preferably has activity complementary to the compound of the present invention, so that they do not adversely affect each other. Such compounds in the combination to appropriately exist in an amount that is effective for planning purpose. In one embodiment, the compound of the present invention is combined with other anti-tumor drugs. The antitumor drugs include: alkylating agents including but not limited to cyclophosphamide, nitrogen mustard, melphalan, chlorambucil, carmostine; platinum metals including but not limited to carboplatin, cisplatin, oxaliplatin; topoisomerase inhibitors including but not limited to topotecan, camptothecin, topotecan, irinotecan; antibiotics including but not limited to anisomycin, actinomycin D, daunorubicin, doxorubicin, mitoxantrone, bleomycin and mithramycin; anti-microtubule or anti-mitotic agents including but not limited to paclitaxel, vinorelbine, docetaxel, doxorubicin; antimetabolites including but not limited to fluorouracil, methotrexate, cytarabine, mecaptopurine, thioguanine and gemcitabine; antibodies including but not limited to herceptin and bevacizumab; hormones including but not limited to letrazole, vorazole, tamoxifen, toremifene, fulvestrant, flutamide, nilutamide and triptorelin; kinase inhibitors such as EGFR kinase inhibitors including but not limited to gefitinib, erlotinib, lapatinib and afatinib; VEGFR inhibitors including but not limited to sorafenib, regorafenib, sunitinib, cabozantinib, pazopanib, vandetanib, axitinib; ALK inhibitors including but not limited to crizotinib, ceritinib and alectinib; Bcr-Abl inhibitors including but not limited to imatinib, ponatinib, nilotinib and dasatinib; BTK inhibitors including but not limited to ibrutinib; B-RAF inhibitors including but not limited to vemurafenib; cyclin-dependent kinase CDK4/6 inhibitor palbociclib; mTOR inhibitors including but not limited to rapamycin and everolimus; deacetylase inhibitors including but not limited to vorinostat; and PD1/PDL1 antibodies such as Keytruda (Pembrolizumab) and Opdivo (Nivolumab).

The fourth aspect of the present invention provides use of the compound, a stereoisomer, a geometric isomer, a tautomer or a pharmaceutically acceptable salt thereof described in the first aspect, or the pharmaceutical composition described in the third aspect in the preparation of a medicament for preventing and/or treating diseases mediated by STAT3, wherein the diseases mediated by STAT3 include cancer, immune diseases, cardiovascular diseases, viral infections, inflammation, metabolic/endocrine dysfunction or neurological diseases.

Beneficial technical effect: the compound of the present invention has high antiproliferative activity in vitro on human prostate cancer cell DU145 with high STAT3 expression. The compound of the present invention shows obvious STAT3 transcription inhibition activity in the STAT3 specific luciferase double reporter gene experiment of human prostate cancer cell DU145, and shows obvious inhibition activity on STAT3 phosphorylation of human prostate cancer DU145 in the western blotting experiment. In vivo pharmacodynamic studies show that the compound of the present invention has a remarkable inhibitory effect on the growth of xenograft tumor formed by subcutaneous xenotransplantation of human prostate cancer DU145 in nude mice.

SPECIFIC MODES FOR CARRYING OUT THE INVENTION

Figure 1:
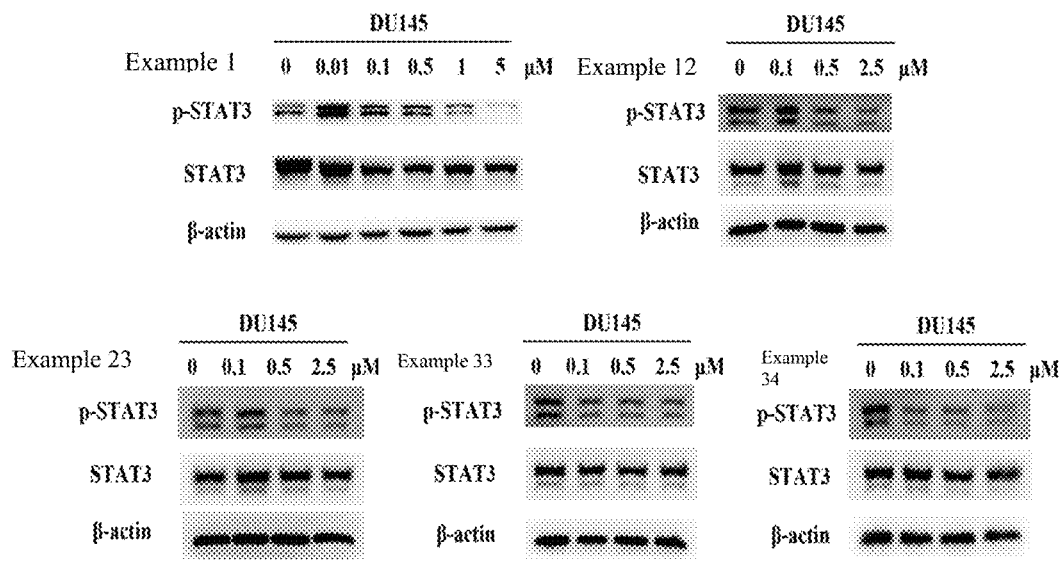
FIG. 1 shows the effects of Examples 12, 23, 33 and 34 on the expression of p-STAT3 of human prostate cancer cell DU145, which shows the inhibitory effects of Examples 12, 23, 33 and 34 on the expression of p-STAT3 of human prostate cancer cell DU145.

The followings are specific examples of the present invention, which further describe the technical solution of the present invention, but the protection scope of the present invention is not limited to these examples. Any change or equivalent substitution that does not depart from the present invention is included in the protection scope of the present invention.

In the following examples, molecule with single chiral center exists in the form of racemic mixture unless structural formula or chemical name is specified otherwise. Molecules with two or more chiral centers exist in form of diastereomer racemic mixture unless structural formula or chemical name is specified otherwise. Single enantiomer/diastereomer can be obtained by methods known to those skilled in the art.

Preparation Method

The compounds of the present invention can be synthesized according to the synthetic scheme in the present invention and/or techniques well known in the art. For example, the compounds provided by the invention can be prepared according to the following general synthetic method.

In a general synthesis method, the compound represented by formula (I) is synthesized according to method-1.

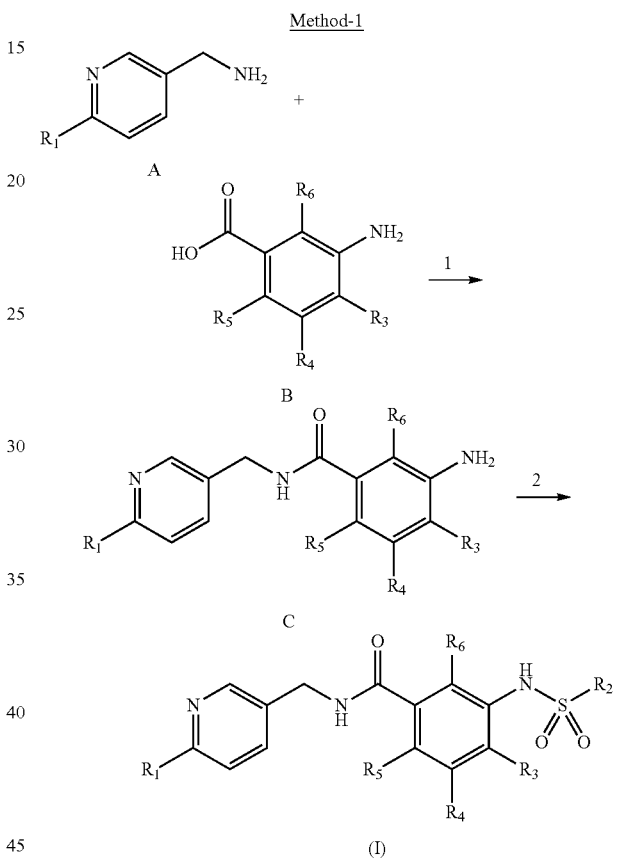

Specifically, in method-1, the benzamide compound of the present invention can be synthesized by 2-step reaction. For example, compound C was obtained from compounds A and B as starting materials via condensation reaction; and the benzamide compound of the present invention was obtained from the compound C via sulfonylation reaction.

In another general synthesis method, the compound represented by formula (I) is synthesized according to method-2.

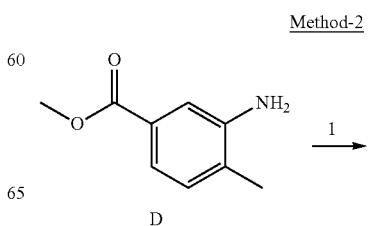

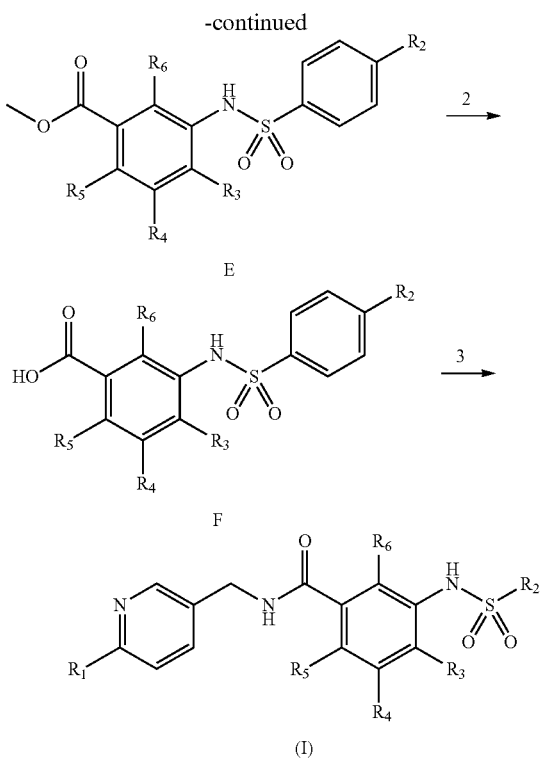

(I)

Specifically, in the general synthesis method-2, the benzamide compound of the present invention can be synthesized by three steps. For example, compound E was obtained from compound D as starting material via sulfonylation reaction, and then compound F was obtained from the compound E via hydrolysis with sodium hydroxide. The benzamide compound of the present invention was obtained by the reaction of the compound F with pyridine-3-methylamine or substituted pyridine-3-methylamine.

The compounds of the present invention can be synthesized according to one or more synthetic schemes and/or techniques well known in the art. Those skilled in the art should realize that the synthetic method of some embodiments described in detail in the present invention can be easily applied to other embodiments. In some embodiments, the compound described herein can be prepared by appropriate combinations of synthetic methods known in the art. Many starting materials and other reagents can be purchased from commercial suppliers, such as Alfa aesar (China) chemical co., LTD., or easily prepared by synthetic methods commonly used in the art.

$^1$H NMR spectra were recorded on instruments operated at 400 MHz or 500 MHz. $^1$H NMR spectra were obtained in solution form (reported as ppm), using CDCl$_3$ (7.26 ppm) or DMSO-d$_6$ (2.50 ppm) or internal standard tetramethylsilane (0.00 ppm) as reference standard. When reporting peak multiplicity, the following abbreviations are used: s (singlet), d (doublet), t (triplet), q (quartet), m (multiplet), br (broad peak), dd (double-doublet), dt (double-triplet). The given coupling constant is measured in Hertz (Hz).

(R)- and (S)-isomers of non-restrictive exemplary compounds, if present, can be separated by methods known to those skilled in the art, if needed, such as can be separated by, for example, crystallization through forming diastereomeric salts or complexes; can be separated by, for example, crystallization or chromatography through forming diastereomeric derivatives; can be separated by allowing one enantiomer to selectively react with an enantiomer-specific reagent, then separating the modified and unmodified enantiomers; or can be separated through chromatographic separation in chiral environment such as chiral chromatographic column. Selectively, specific enantiomers can be prepared by asymmetric synthesis using optically-active reagents, substrates, catalysts or solvents, or prepared by converting one enantiomer into another one through asymmetric conversion.

In the following preparative methods and examples, "Me" refers to methyl, "Et" refers to ethyl, "PE" refers to petroleum ether, "EtOAc" refers to ethyl acetate, "MeOH" refers to methanol, "DMSO-d$_6$" refers to deuterated dimethyl sulfoxide, "DCM" refers to methylene chloride, "DMAP" refers to 4-dimethylaminopyridine, "HATU" refers to O-(7-azabenzotriazolyl)-N,N,N',N'-tetramethyluronium hexafluorophosphate, "rt" refers to room temperature, "mL" refers to milliliters, "mmol" refers to millimoles, "μM" refers to micromoles, "nM" refers to nanomoles, and "° C." refers to degrees Celsius.

Example 1: Preparation of 4-methyl-3-((4-methylphenyl) sulfonamido)-N-(pyridin-3-ylmethyl) benzamide

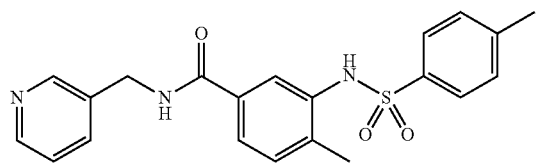 [SMILES: Cc1ccc(S(=O)(=O)Nc2cc(C(=O)NCc3cccnc3)ccc2C)cc1]

Step 1: Preparation of 3-amino-4-methyl-N-(pyridin-3-ylmethyl) benzamide

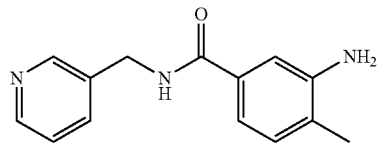 [SMILES: Cc1ccc(C(=O)NCc2cccnc2)cc1N]

A reaction mixture of 3-amino-4-methylbenzoic acid (3.02 g, 20 mmol), pyridin-3-ylmethylamine (3.24 g, 30 mmol), HATU(9.12 g, 24 mmol) and triethylamine (6.07 g, 60 mmol) in DCM (150 mL) was stirred overnight. Water (100 mL) was added and the resulting suspension was stirred vigorously for 10 minutes. The resulting yellow solid was collected by suction filtration, washed with water (50 mL×2) and DCM (30 mL×3), and dried to obtain a yellow solid (4.02 g, yield 83%).

$^1$H NMR (400 MHz, DMSO-d$_6$) δ 8.79 (t, J=6.0 Hz, 1H), 8.53 (d, J=1.8 Hz, 1H), 8.44 (dd, J=4.8, 1.6 Hz, 1H), 7.69 (dt, J=7.8, 1.9 Hz, 1H), 7.34 (ddd, J=7.8, 4.8, 0.8 Hz, 1H), 7.11 (s, 1H), 7.02-6.94 (m, 2H), 4.99 (s, 2H), 4.44 (d, J=6.0 Hz, 2H), 2.08 (s, 3H).

Step 2: Preparation of 4-methyl-3-((4-methylphenyl)sulfonamido)-N-(pyridin-3-ylmethyl) benzamide

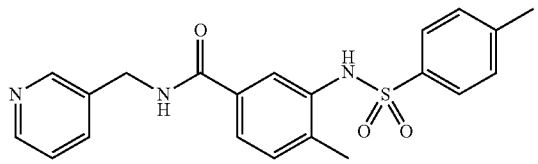 [SMILES: Cc1ccc(S(=O)(=O)Nc2cc(C(=O)NCc3cccnc3)ccc2C)cc1]

A mixture of 3-amino-4-methyl-N-(pyridin-3-ylmethyl) benzamide (121 mg, 0.5 mmol), p-toluenesulfonyl chloride (111 mg, 0.6 mmol), pyridine (59 mg, 0.75 mmol) and DMAP(12 mg, 0.1 mmol) in DCM (10 mL) was stirred overnight at room temperature. Water (50 mL) was added, and the resulting mixture was extracted with DCM (30 mL×3). The combined organic layers were washed with water (30 mL×2) and saline (30 mL), dried with anhydrous sodium sulfate, filtered and concentrated. The residue was purified by preparative thin layer chromatography (silica gel, DCM/MEOH=15:1) to obtain a yellow foamy solid (132 mg, yield 63%).

$^1$H NMR (400 MHz, DMSO-d$_6$) δ 9.64 (s, 1H), 9.02 (t, J=5.9 Hz, 1H), 8.53 (d, J=1.8 Hz, 1H), 8.46 (dd, J=4.8, 1.6 Hz, 1H), 7.70 (dt, J=7.8, 1.9 Hz, 1H), 7.66-7.57 (m, 2H), 7.52 (d, J=8.3 Hz, 2H), 7.39-7.36 (m, 1H), 7.33 (d, J=8.1 Hz, 2H), 7.21 (d, J=7.7 Hz, 1H), 4.45 (d, J=5.8 Hz, 2H), 2.35 (s, 3H), 1.95 (s, 3H).

Example 2: 3-((4-methylphenyl)sulfonamido)-N-(pyridin-3-ylmethyl)benzamide

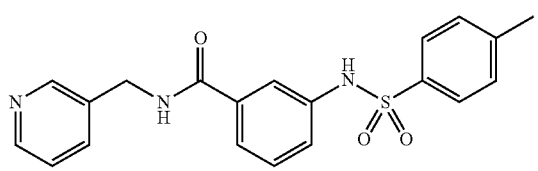 [SMILES: Cc1ccc(S(=O)(=O)Nc2cccc(C(=O)NCc3cccnc3)c2)cc1]

Step 1: Preparation of 3-amino-N-(pyridin-3-ylmethyl)benzamide

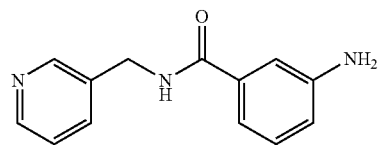 [SMILES: Nc1cccc(C(=O)NCc2cccnc2)c1]

According to the method of step 1 in Example 1, the title compound was synthesized from 3-aminobenzoic acid.

$^1$H NMR (400 MHz, DMSO-d$_6$) δ 8.85 (t, J=5.9 Hz, 1H), 8.53 (d, J=1.2 is Hz, 1H), 8.45 (dd, J=4.5, 1.1 Hz, 1H), 7.74-7.67 (m, 1H), 7.36 (ddd, J=7.7, 4.7, 0.4 Hz, 1H), 7.08 (t, J=7.8 Hz, 1H), 7.05 (t, J=2.0 Hz, 1H), 7.00-6.96 (m, 1H), 6.69 (ddd, J=7.9, 2.3, 1.0 Hz, 1H), 5.31 (br s, 2H), 4.44 (d, J=5.9 Hz, 2H).

MS (ESI+) m/z 228.0 [M+H]+.

Step 2: Preparation of 3-((4-methylphenyl)sulfonamido)-N-(pyridin-3-ylmethyl) benzamide

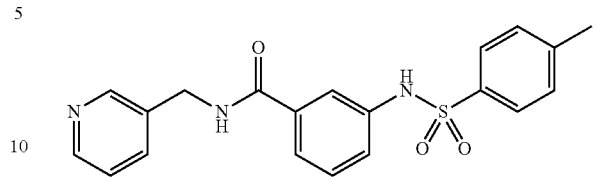

According to the method of step 2 in Example 1, the title compound was synthesized from 3-amino-N-(pyridin-3-ylmethyl) benzamide.

$^1$H NMR (400 MHz, DMSO-d$_6$) δ 10.39 (s, 1H), 9.05 (t, J=5.7 Hz, 1H), 8.61-8.39 (m, 2H), 7.78-7.59 (m, 4H), 7.52 (dd, J=7.7, 1.1 Hz, 1H), 7.45-7.29 (m, 4H), 7.28-7.21 (m, 1H), 4.45 (d, J=5.7 Hz, 2H), 2.32 (s, 3H).

Example 3: 4-fluoro-3-((4-methylphenyl) sulfonamido)-N-(pyridin-3-ylmethyl) benzamide

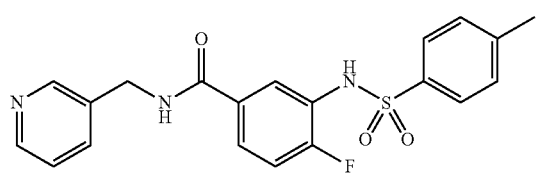 [SMILES: Cc1ccc(S(=O)(=O)Nc2cc(C(=O)NCc3cccnc3)ccc2F)cc1]

Step 1: Preparation of 3-amino-4-fluoro-N-(pyridin-3-ylmethyl) benzamide

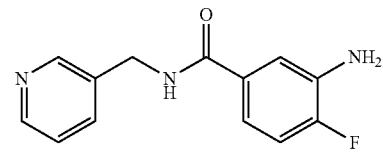 [SMILES: Nc1cc(C(=O)NCc2cccnc2)ccc1F]

According to the method of step 1 in Example 1, the title compound was synthesized from 3-amino-4-fluorobenzoic acid.

$^1$H NMR (400 MHz, DMSO-d$_6$) δ 8.90 (t, J=5.7 Hz, 1H), 8.53 (s, 1H), 8.46 (d, J=4.6 Hz, 1H), 7.70 (dt, J=7.8, 1.8 Hz, 1H), 7.35 (dd, J=7.8, 4.7 Hz, 1H), 7.32-7.26 (m, 1H), 7.10-7.01 (m, 2H), 5.34 (br s, 2H), 4.44 (d, J=5.9 Hz, 2H).

MS (ESI+) m/z 245.9 [M+H]+.

Step 2: Preparation of 4-fluoro-3-((4-methylphenyl) sulfonamido)-N-(pyridin-3-ylmethyl)benzamide

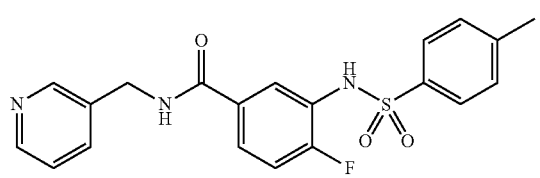 [SMILES: Cc1ccc(S(=O)(=O)Nc2cc(C(=O)NCc3cccnc3)ccc2F)cc1]

According to the synthesis method of step 2 in Example 1, the title compound was synthesized from 3-amino-4-fluoro-N-(pyridin-3-ylmethyl) benzamide.

$^1$H NMR (400 MHz, DMSO-d$_6$) δ 10.26 (s, 1H), 9.12 (t, J=5.9 Hz, 1H), 8.54 (s, 1H), 8.47 (d, J=4.0 Hz, 1H), 7.86 (dd, J=7.7, 2.2 Hz, 1H), 7.75-7.67 (m, 2H), 7.60 (d, J=8.3 Hz, 2H), 7.40-7.31 (m, 3H), 7.26 (dd, J=10.0, 8.6 Hz, 1H), 4.46 (d, J=5.8 Hz, 2H), 2.35 (s, 3H).

Example 4: 4-chloro-3-((4-methylphenyl)sulfonamido)-N-(pyridin-3-ylmethyl) benzamide

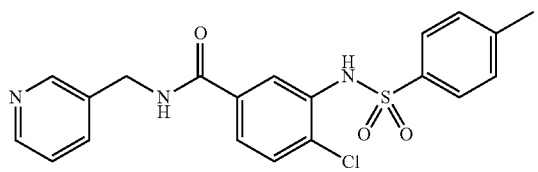 [SMILES: Cc1ccc(S(=O)(=O)Nc2cc(C(=O)NCc3cccnc3)ccc2Cl)cc1]

Step 1: Preparation of 3-amino-4-chloro-N-(pyridin-3-ylmethyl)benzamide

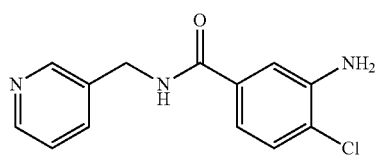 [SMILES: Nc1cc(C(=O)NCc2cccnc2)ccc1Cl]

According to the method of step 1 in Example 1, the title compound was synthesized from 3-amino-4-chlorobenzoic acid.

$^1$H NMR (400 MHz, DMSO-d$_6$) δ 8.95 (t, J=5.9 Hz, 1H), 8.53 (d, J=1.7 Hz, 1H), 8.45 (dd, J=4.8, 1.6 Hz, 1H), 7.74-7.65 (m, 1H), 7.35 (ddd, J=7.8, 4.8, 0.7 Hz, 1H), 7.29 (d, J=2.1 Hz, 1H), 7.27 (d, J=8.3 Hz, 1H), 7.02 (dd, J=8.3, 2.1 Hz, 1H), 5.53 (br s, 2H), 4.45 (d, J=5.9 Hz, 2H).

MS (ESI+) m/z 261.9 [M+H]+.

Step 2: Preparation of 4-chloro-3-((4-methylphenyl)sulfonamido)-N-(pyridin-3-ylmethyl)benzamide

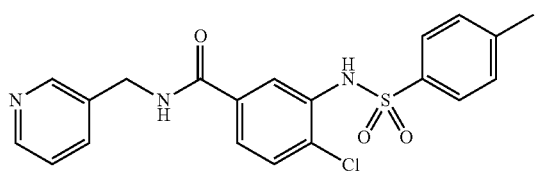 [SMILES: Cc1ccc(S(=O)(=O)Nc2cc(C(=O)NCc3cccnc3)ccc2Cl)cc1]

According to the method of step 2 in Example 1, the title compound was synthesized from 4-chloro-3-((4-methylphenyl) sulfonamido) benzoic acid.

$^1$H NMR (400 MHz, DMSO-d$_6$) δ 10.08 (s, 1H), 9.18 (t, J=5.8 Hz, 1H), 8.54 (d, J=1.6 Hz, 1H), 8.47 (dd, J=4.7, 1.4 Hz, 1H), 7.85 (d, J=2.1 Hz, 1H), 7.75-7.66 (m, 2H), 7.59 (d, J=8.3 Hz, 2H), 7.51 (d, J=8.4 Hz, 1H), 7.40-7.31 (m, 3H), 4.47 (d, J=5.8 Hz, 2H), 2.36 (s, 3H).

Example 5: Preparation of 4-methoxy-3-((4-methylphenyl)sulfonamido)-N-(pyridin-3-ylmethyl)benzamide

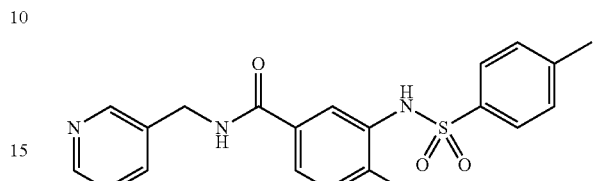

Step 1: Preparation of 3-amino-4-methoxy-N-(pyridin-3-ylmethyl)benzamide

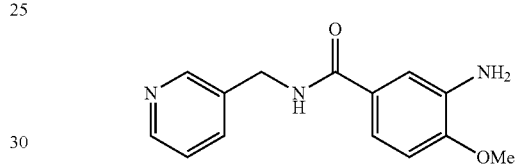

According to the method of step 1 in Example 1, the title compound was synthesized from 3-amino-4-methoxybenzoic acid.

$^1$H NMR (400 MHz, DMSO-d$_6$) δ 8.75 (t, J=5.9 Hz, 1H), 8.52 (d, J=1.8 Hz, 1H), 8.44 (dd, J=4.7, 1.5 Hz, 1H), 7.73-7.65 (m, 1H), 7.38-7.31 (m, 1H), 7.17 (d, J=2.2 Hz, 1H), 7.11 (dd, J=8.3, 2.2 Hz, 1H), 6.83 (d, J=8.4 Hz, 1H), 4.85 (s, 2H), 4.43 (d, J=5.9 Hz, 2H), 3.80 (s, 3H).

Step 2: Preparation of 4-methoxy-3-((4-methylphenyl)sulfonamido)-N-(pyridin-3-ylmethyl)benzamide

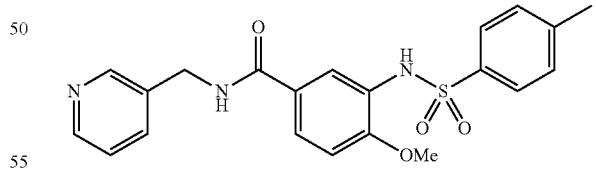

According to the method of step 2 in Example 1, the title compound was synthesized from 3-amino-4-methoxy-N-(pyridin-3-ylmethyl) benzamide.

$^1$H NMR (400 MHz, DMSO-d$_6$) δ 9.52 (s, 1H), 8.97 (t, J=5.8 Hz, 1H), 8.53 (d, J=2.0 Hz, 1H), 8.46 (dd, J=4.8, 1.5 Hz, 1H), 7.82 (d, J=2.2 Hz, 1H), 7.74-7.66 (m, 2H), 7.57 (d, J=8.3 Hz, 2H), 7.36 (dd, J=7.8, 4.8 Hz, 1H), 7.31 (d, J=8.3 Hz, 2H), 6.96 (d, J=8.7 Hz, 1H), 4.45 (d, J=5.9 Hz, 2H), 3.52 (s, 3H), 2.34 (s, 3H).

Example 6: 4-ethyl-3-((4-methylphenyl)sulfonamido)-N-(pyridin-3-ylmethyl)benzamide

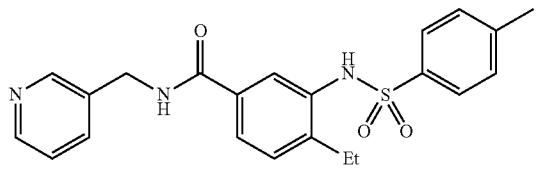 [SMILES: CCc1ccc(C(=O)NCc2cccnc2)cc1NS(=O)(=O)c1ccc(C)cc1]

Step 1: Preparation of 3-amino-4-ethyl-N-(pyridin-3-ylmethyl)benzamide

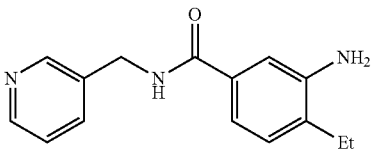 [SMILES: CCc1ccc(C(=O)NCc2cccnc2)cc1N]

According to the method of step 1 in Example 1, the title compound was synthesized from 3-amino-4-ethylbenzoic acid.

$^1$H NMR (400 MHz, DMSO-d$_6$) δ 8.81 (t, J=6.0 Hz, 1H), 8.52 (d, J=1.7 Hz, 1H), 8.45 (dd, J=4.7, 1.5 Hz, 1H), 7.73-7.65 (m, 1H), 7.39-7.31 (m, 1H), 7.11 (d, J=1.6 Hz, 1H), 7.04-6.95 (m, 2H), 5.03 (s, 2H), 4.44 (d, J=6.0 Hz, 2H), 2.46 (q, J=7.5 Hz, 2H), 1.12 (t, J=7.5 Hz, 3H).

Step 2: Preparation of 4-ethyl-3-((4-methylphenyl)sulfonamido)-N-(pyridin-3-ylmethyl)benzamide

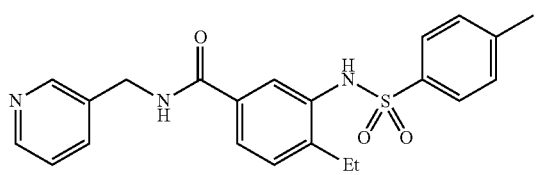 [SMILES: CCc1ccc(C(=O)NCc2cccnc2)cc1NS(=O)(=O)c1ccc(C)cc1]

According to the synthesis method of step 2 in Example 1, the title compound was synthesized from 3-amino-4-ethyl-N-(pyridin-3-ylmethyl) benzamide.

$^1$H NMR (400 MHz, DMSO-d$_6$) δ 9.64 (s, 1H), 9.00 (t, J=5.9 Hz, 1H), 8.52 (d, J=2.0 Hz, 1H), 8.46 (dd, J=4.8, 1.6 Hz, 1H), 7.71-7.64 (m, 2H), 7.57-7.51 (m, 3H), 7.39-7.31 (m, 3H), 7.27 (d, J=8.1 Hz, 1H), 4.45 (d, J=5.9 Hz, 2H), 2.44 (q, J=7.5 Hz, 2H), 2.35 (s, 3H), 0.92 (t, J=7.5 Hz, 3H).

Example 7: 3-methyl-5-((4-methylphenyl)sulfonamido)-N-(pyridin-3-ylmethyl)benzamide

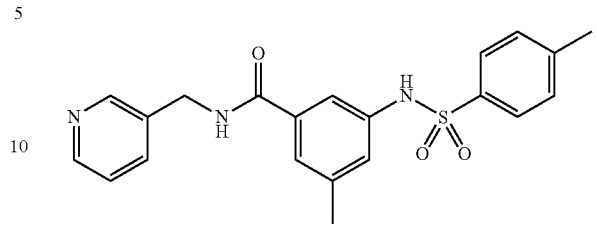

Step 1: Preparation of 3-amino-5-methyl-N-(pyridin-3-ylmethyl)benzamide

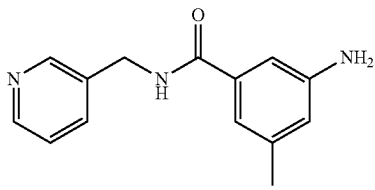 [SMILES: Cc1cc(N)cc(C(=O)NCc2cccnc2)c1]

According to the method of step 1 in Example 1, the title compound was synthesized from 3-amino-5-methylbenzoic acid.

$^1$H NMR (400 MHz, DMSO-d$_6$) δ 8.81 (t, J=6.0 Hz, 1H), 8.53 (d, J=1.7 Hz, 1H), 8.45 (dd, J=4.8, 1.6 Hz, 1H), 7.70 (ddd, J=7.9, 2.1, 1.7 Hz, 1H), 7.36 (ddd, J=7.8, 4.8, 0.8 Hz, 1H), 6.86 (t, J=1.7 Hz, 1H), 6.84-6.81 (m, 1H), 6.58-6.48 (m, 1H), 5.29 (br s, 2H), 4.43 (d, J=6.0 Hz, 2H), 2.20 (s, 3H).

MS (ESI+) m/z 242.2 [M+H]+.

Step 2: Preparation of 3-methyl-5-(4-methylphenyl)sulfonamido)-N-(pyridin-3-ylmethyl)benzamide

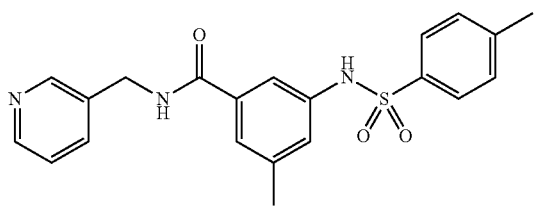 [SMILES: Cc1ccc(S(=O)(=O)Nc2cc(C)cc(C(=O)NCc3cccnc3)c2)cc1]

According to the method of step 2 in Example 1, the title compound was synthesized from 3-amino-5-methyl-N-(pyridin-3-ylmethyl) benzamide.

$^1$H NMR (400 MHz, DMSO-d$_6$) δ 10.32 (s, 1H), 8.99 (t, J=5.9 Hz, 1H), 8.52 (d, J=1.8 Hz, 1H), 8.46 (dd, J=4.7, 1.6 Hz, 1H), 7.73-7.59 (m, 3H), 7.41 (t, J=1.6 Hz, 1H), 7.38-7.30 (m, 4H), 7.10-7.05 (m, 1H), 4.43 (d, J=5.9 Hz, 2H), 2.32 (s, 3H), 2.24 (s, 3H).

MS (ESI+) m/z 396.3 [M+H]+.

Example 8: 3-methoxy-5-((4-methylphenyl)sulfonamido)-N-(pyridin-3-ylmethyl)benzamide

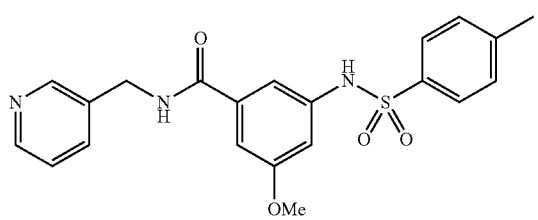 [SMILES: COc1cc(NS(=O)(=O)c2ccc(C)cc2)cc(C(=O)NCc2cccnc2)c1]

Step 1: Preparation of 3-amino-5-methoxy-N-(pyridin-3-ylmethyl)benzamide

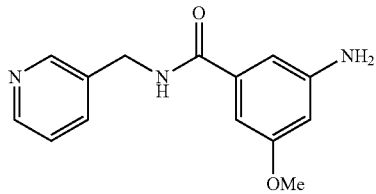 [SMILES: COc1cc(N)cc(C(=O)NCc2cccnc2)c1]

According to the method of step 1 in Example 1, the title compound was synthesized from 3-amino-5-methoxybenzoic acid.

$^1$H NMR (400 MHz, DMSO-d$_6$) δ 8.84 (t, J=6.0 Hz, 1H), 8.53 (d, J=1.2 Hz, 1H), 8.45 (dd, J=4.6, 1.2 Hz, 1H), 7.70 (ddd, J=7.9, 2.1, 1.7 Hz, 1H), 7.36 (ddd, J=7.8, 4.8, 0.7 Hz, 1H), 6.71-6.63 (m, 1H), 6.58 (dd, J=2.3, 1.5 Hz, 1H), 6.28 (t, J=2.1 Hz, 1H), 5.33 (s, 2H), 4.44 (d, J=5.9 Hz, 2H), 3.70 (s, 3H).

Step 2: Preparation of 3-methoxy-5-((4-methylphenyl)sulfonamido)-N-(pyridin-3-ylmethyl)benzamide

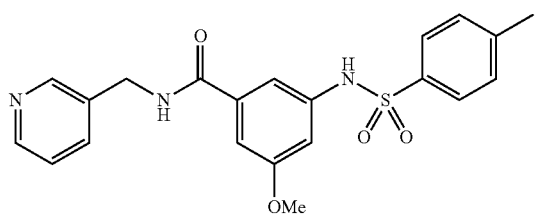 [SMILES: COc1cc(NS(=O)(=O)c2ccc(C)cc2)cc(C(=O)NCc2cccnc2)c1]

According to the method of step 2 in Example 1, the title compound was synthesized from 3-amino-5-methoxy-N-(pyridin-3-ylmethyl) benzamide.

$^1$H NMR (400 MHz, DMSO-d$_6$) δ 10.44 (s, 1H), 9.22 (t, J=5.3 Hz, 1H), 8.78 (s, 1H), 8.72 (d, J=5.3 Hz, 1H), 8.26 (d, J=6.1 Hz, 1H), 7.90-7.79 (m, 1H), 7.73-7.61 (m, 2H), 7.35 (d, J=7.9 Hz, 2H), 7.26-7.18 (m, 1H), 7.15 (s, 1H), 6.83 (t, J=2.1 Hz, 1H), 4.56 (d, J=5.7 Hz, 2H), 3.73 (s, 3H), 2.33 (s, 3H).

Example 9: 3-fluoro-5-((4-methylphenyl)sulfonamido)-N-(pyridin-3-ylmethyl)benzamide

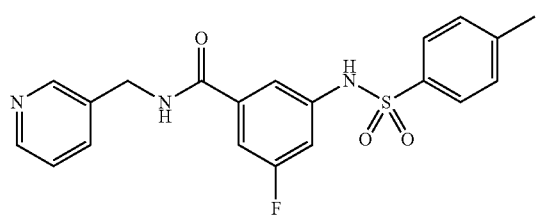 [SMILES: Cc1ccc(S(=O)(=O)Nc2cc(F)cc(C(=O)NCc3cccnc3)c2)cc1]

Step 1: Preparation of 3-amino-5-fluoro-N-(pyridin-3-ylmethyl)benzamide

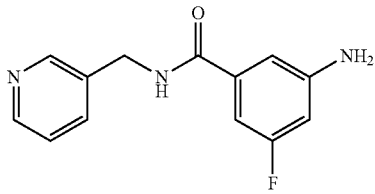 [SMILES: Nc1cc(F)cc(C(=O)NCc2cccnc2)c1]

According to the method of step 1 in Example 1, the title compound was synthesized from 3-amino-5-fluorobenzoic acid.

$^1$H NMR (400 MHz, DMSO-d$_6$) δ 8.93 (t, J=5.9 Hz, 1H), 8.53 (d, J=1.8 Hz, 1H), 8.46 (dd, J=4.8, 1.6 Hz, 1H), 7.76-7.65 (m, 1H), 7.36 (ddd, J=7.9, 4.8, 0.7 Hz, 1H), 6.92-6.84 (m, 1H), 6.74 (ddd, J=9.8, 2.3, 1.5 Hz, 1H), 6.45 (dt, J=11.4, 2.2 Hz, 1H), 5.64 (br s, 2H), 4.44 (d, J=5.9 Hz, 2H).

MS (ESI+) m/z 246.2 [M+H]+.

Step 2: Preparation of 3-fluoro-5-((4-methylphenyl)sulfonamido)-N-(pyridin-3-ylmethyl)benzamide

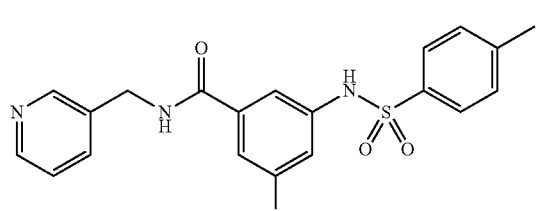

According to the method of step 2 in Example 1, the title compound was synthesized from 3-amino-5-fluoro-N-(pyridin-3-ylmethyl) benzamide.

$^1$H NMR (400 MHz, DMSO-d$_6$) δ 10.82 (s, 1H), 9.42 (t, J=4.7 Hz, 1H), 8.87 (s, 1H), 8.80 (d, J=5.5 Hz, 1H), 8.44 (d, J=8.0 Hz, 1H), 8.03-7.91 (m, 1H), 7.77-7.64 (m, 2H), 7.47 (dd, J=10.9, 1.5 Hz, 2H), 7.37 (d, J=8.4 Hz, 2H), 7.11 (dt, J=10.4, 2.1 Hz, 1H), 4.60 (d, J=5.7 Hz, 2H), 2.34 (s, 3H).

MS (ESI+) m/z 400.3 [M+H]+.

Example 10: 3-chloro-5-((4-methylphenyl)sulfonamido)-N-(pyridin-3-ylmethyl)benzamide

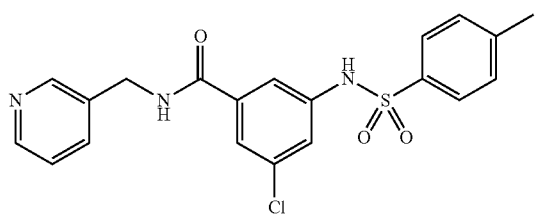 [SMILES: Cc1ccc(S(=O)(=O)Nc2cc(Cl)cc(C(=O)NCc3cccnc3)c2)cc1]

Step 1: Preparation of 3-amino-5-chloro-N-(pyridin-3-ylmethyl)benzamide

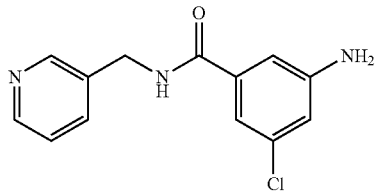 [SMILES: Nc1cc(Cl)cc(C(=O)NCc2cccnc2)c1]

According to the method of step 1 in Example 1, the title compound was synthesized from 3-amino-5-chlorobenzoic acid.

$^1$H NMR (400 MHz, DMSO-d$_6$) δ 8.98 (t, J=5.9 Hz, 1H), 8.53 (d, J=1.4 Hz, 1H), 8.46 (d, J=4.6 Hz, 1H), 7.70 (d, J=7.8 Hz, 1H), 7.36 (dd, J=7.8, 4.8 Hz, 1H), 7.04-6.96 (m, 2H), 6.72 (t, J=1.9 Hz, 1H), 5.64 (br s, 2H), 4.44 (d, J=5.9 Hz, 2H).

MS (ESI+) m/z 262.2 [M+H]+.

Step 2: Preparation of 3-chloro-5-((4-methylphenyl)sulfonamido)-N-(pyridin-3-ylmethyl)benzamide

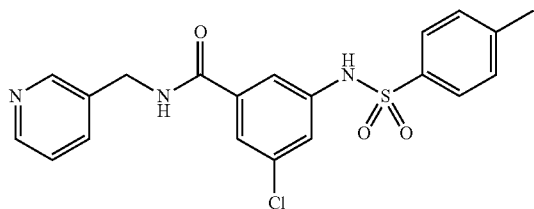

According to the method of step 2 in Example 1, the title compound was synthesized from 3-amino-5-chloro-N-(pyridin-3-ylmethyl) benzamide.

$^1$H NMR (400 MHz, DMSO-d$_6$) δ 10.77 (s, 1H), 9.31 (t, J=5.8 Hz, 1H), 8.76 (d, J=1.4 Hz, 1H), 8.70 (dd, J=5.3, 1.0 Hz, 1H), 8.21 (d, J=8.0 Hz, 1H), 7.78 (dd, J=7.9, 5.4 Hz, 1H), 7.71-7.66 (m, 2H), 7.65 (t, J=1.7 Hz, 1H), 7.59 (dd, J=2.0, 1.5 Hz, 1H), 7.38 (dd, J=8.5, 0.5 Hz, 2H), 7.29 (t, J=2.0 Hz, 1H), 4.55 (d, J=5.7 Hz, 2H), 2.34 (s, 3H).

MS (ESI+) m/z 416.3 [M+H]+.

Example 11: 2-methyl-5-((4-methylphenyl)sulfonamido)-N-(pyridin-3-ylmethyl)benzamide

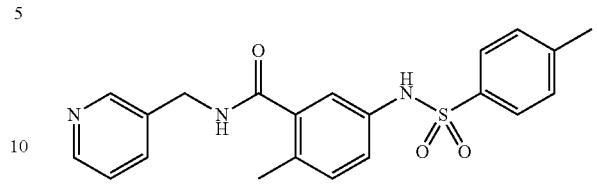

Step 1: Preparation of 5-amino-2-methyl-N-(pyridin-3-ylmethyl)benzamide

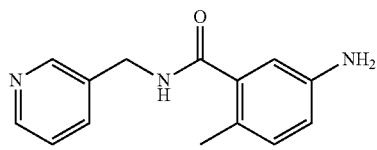 [SMILES: Cc1ccc(N)cc1C(=O)NCc1cccnc1]

According to the method of step 1 in Example 1, the title compound was synthesized from 5-amino-2-methylbenzoic acid.

$^1$H NMR (400 MHz, DMSO-d$_6$) δ 8.70 (t, J=6.0 Hz, 1H), 8.55 (d, J=1.8 Hz, 1H), 8.46 (dd, J=4.7, 1.4 Hz, 1H), 7.76-7.68 (m, 1H), 7.37 (ddd, J=7.9, 4.8, 0.7 Hz, 1H), 6.86 (d, J=8.1 Hz, 1H), 6.58 (d, J=2.4 Hz, 1H), 6.53 (dd, J=8.1, 2.5 Hz, 1H), 5.03 (s, 2H), 4.41 (d, J=6.0 Hz, 2H), 2.12 (s, 3H).

MS (ESI+) m/z 242.2 [M+H]+.

Step 2: Preparation of 2-methyl-5-((4-methylphenyl)sulfonamido)-N-(pyridin-3-ylmethyl)benzamide

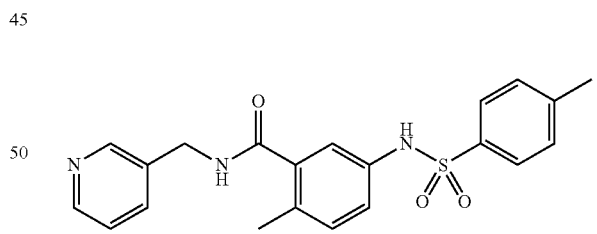

According to the method of step 1 in Example 1, the title compound was synthesized from 5-amino-2-methyl-N-(pyridin-3-ylmethyl) benzamide.

$^1$H NMR (400 MHz, DMSO-d$_6$) δ 10.24 (s, 1H), 8.82 (t, J=6.0 Hz, 1H), 8.56-8.51 (m, 1H), 8.48 (dd, J=4.8, 1.6 Hz, 1H), 7.73-7.67 (m, 1H), 7.67-7.60 (m, 2H), 7.38 (ddd, J=7.8, 4.8, 0.7 Hz, 1H), 7.36-7.31 (m, 2H), 7.11-7.02 (m, 3H), 4.42 (d, J=6.0 Hz, 2H), 2.33 (s, 3H), 2.16 (s, 3H).

MS (ESI+) m/z 396.3 [M+H]+.

Example 12: 3-((4-ethylphenyl)sulfonamido)-4-methyl-N-(pyridin-3-ylmethyl)benzamide

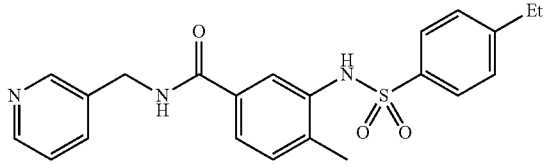 [SMILES: CCc1ccc(S(=O)(=O)Nc2cc(C(=O)NCc3cccnc3)ccc2C)cc1]

According to the method of step 2 in Example 1, the title compound was synthesized from 3-amino-4-methyl-N-(pyridin-3-ylmethyl) benzamide and p-ethylbenzenesulfonyl chloride.

$^1$H NMR (400 MHz,) δ 9.65 (s, 1H), 9.04 (t, J=6.0 Hz, 1H), 8.53 (d, J=2.0 Hz, 1H), 8.46 (dd, J=4.8, 1.6 Hz, 1H), 7.70 (dt, J=7.9, 2.0 Hz, 1H), 7.65-7.60 (m, 2H), 7.58-7.53 (m, 2H), 7.40-7.33 (m, 3H), 7.21 (d, J=8.0 Hz, 1H), 4.45 (d, J=6.0 Hz, 2H), 2.65 (d, J=7.6 Hz, 2H), 1.95 (s, 3H), 1.16 (t, J=7.6 Hz, 3H).

Example 13: 3-((4-methoxyphenyl)sulfonamido)-4-methyl-N-(pyridin-3-ylmethyl)benzamide

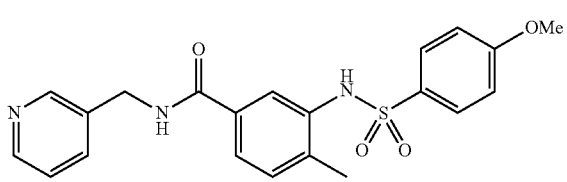 [SMILES: COc1ccc(S(=O)(=O)Nc2cc(C(=O)NCc3cccnc3)ccc2C)cc1]

According to the method of step 2 in Example 1, the title compound was synthesized from 3-amino-4-methyl-N-(pyridin-3-ylmethyl) benzamide and 4-methoxybenzenesulfonyl chloride.

$^1$H NMR (400 MHz, DMSO-$d_6$) δ 9.55 (s, 1H), 9.02 (t, J=5.9 Hz, 1H), 8.53 (s, 1H), 8.46 (d, J=4.2 Hz, 1H), 7.69 (d, J=7.9 Hz, 1H), 7.66-7.59 (m, 2H), 7.56 (d, J=8.9 Hz, 2H), 7.36 (dd, J=7.8, 4.8 Hz, 1H), 7.21 (d, J=8.0 Hz, 1H), 7.05 (d, J=8.9 Hz, 2H), 4.45 (d, J=5.8 Hz, 2H), 3.80 (s, 3H), 1.97 (s, 3H).

Example 14: 3-((3-methoxyphenyl)sulfonamido)-4-methyl-N-(pyridin-3-ylmethyl)benzamide

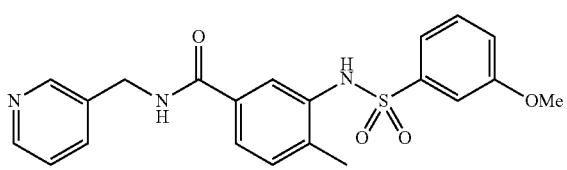 [SMILES: COc1cccc(S(=O)(=O)Nc2cc(C(=O)NCc3cccnc3)ccc2C)c1]

According to the method of step 2 in Example 1, the title compound was synthesized from 3-amino-4-methyl-N-(pyridin-3-ylmethyl) benzamide and 3-methoxybenzenesulfonyl chloride.

$^1$H NMR (400 MHz, DMSO-$d_6$) δ 9.72 (s, 1H), 9.03 (t, J=5.9 Hz, 1H), 8.53 (d, J=1.8 Hz, 1H), 8.46 (dd, J=4.8, 1.6 Hz, 1H), 7.69 (dt, J=7.9, 1.9 Hz, 1H), 7.64 (dd, J=7.8, 1.8 Hz, 1H), 7.61 (d, J=1.7 Hz, 1H), 7.46 (t, J=8.0 Hz, 1H), 7.36 (ddd, J=7.8, 4.7, 0.6 Hz, 1H), 7.26-7.17 (m, 3H), 7.15-7.10 (m, 1H), 4.45 (d, J=5.9 Hz, 2H), 3.73 (s, 3H), 1.99 (s, 3H). MS (ESI+) m/z 412.3 [M+H]+.

Example 15: 3-((4-ethoxyphenyl)sulfonamido)-4-methyl-N-(pyridin-3-ylmethyl)benzamide

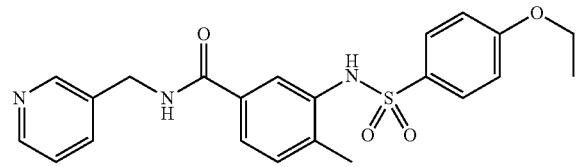 [SMILES: CCOc1ccc(S(=O)(=O)Nc2cc(C(=O)NCc3cccnc3)ccc2C)cc1]

According to the method of step 2 in Example 1, the title compound was synthesized from 3-amino-4-methyl-N-(pyridin-3-ylmethyl) benzamide and 4-ethoxybenzenesulfonyl chloride.

$^1$H NMR (400 MHz, DMSO-$d_6$) δ 9.57 (s, 1H), 9.04 (t, J=5.8 Hz, 1H), 8.53 (d, J=1.4 Hz, 1H), 8.46 (dd, J=4.6, 1.2 Hz, 1H), 7.69 (dt, J=7.9, 1.9 Hz, 1H), 7.66-7.58 (m, 2H), 7.54 (d, J=8.9 Hz, 2H), 7.40-7.32 (m, 1H), 7.21 (d, J=7.9 Hz, 1H), 7.03 (d, J=9.0 Hz, 2H), 4.45 (d, J=5.9 Hz, 2H), 4.07 (q, J=7.0 Hz, 2H), 1.96 (s, 3H), 1.32 (t, J=7.0 Hz, 3H).

Example 16: 3-((3,4-dimethylphenyl)sulfonamido)-4-methyl-N-(pyridin-3-ylmethyl)benzamide

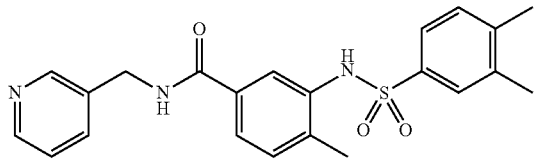 [SMILES: Cc1ccc(S(=O)(=O)Nc2cc(C(=O)NCc3cccnc3)ccc2C)cc1C]

According to the method of step 2 in Example 1, the title compound was synthesized from 3-amino-4-methyl-N-(pyridin-3-ylmethyl) benzamide and 3,4-dimethylbenzenesulfonyl chloride.

$^1$H NMR (400 MHz, DMSO-$d_6$) δ 9.58 (s, 1H), 9.02 (t, J=5.9 Hz, 1H), 8.52 (d, J=1.2 Hz, 1H), 8.46 (dd, J=4.7, 1.1 Hz, 1H), 7.69 (dt, J=7.8, 1.8 Hz, 1H), 7.65-7.58 (m, 2H), 7.42 (s, 1H), 7.39-7.33 (m, 2H), 7.29 (d, J=8.0 Hz, 1H), 7.22 (d, J=8.4 Hz, 1H), 4.45 (d, J=5.8 Hz, 2H), 2.26 (s, 3H), 2.22 (s, 3H), 1.99 (s, 3H).

Example 17: 3-((2,4-dimethylphenyl)sulfonamido)-4-methyl-N-(pyridin-3-ylmethyl)benzamide

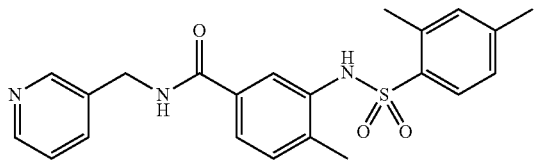 [SMILES: Cc1ccc(S(=O)(=O)Nc2cc(C(=O)NCc3cccnc3)ccc2C)c(C)c1]

According to the method of step 2 in Example 1, the title compound was synthesized from 3-amino-4-methyl-N-(pyridin-3-ylmethyl) benzamide and 2,4-dimethylbenzenesulfonyl chloride.

$^1$H NMR (400 MHz, DMSO-d$_6$) δ 9.66 (s, 1H), 9.00 (t, J=5.9 Hz, 1H), 8.52 (d, J=0.8 Hz, 1H), 8.49 (t, J=4.8, 0.8 Hz, 1H), 7.68 (dt, J=7.7, 1.7 Hz, 1H), 7.65-7.57 (m, 2H), 7.51 (d, J=8.1 Hz, 1H), 7.36 (dd, J=7.8, 4.8 Hz, 1H), 7.26-7.17 (m, 2H), 7.08 (d, J=8.0 Hz, 1H), 4.44 (d, J=5.8 Hz, 2H), 2.50 (s, 3H), 2.30 (s, 3H), 2.01 (s, 3H).

Example 18: 4-methyl-N-(pyridin-3-ylmethyl)-3-((4-(trifluoromethyl)phenyl) sulfonamido)benzamide

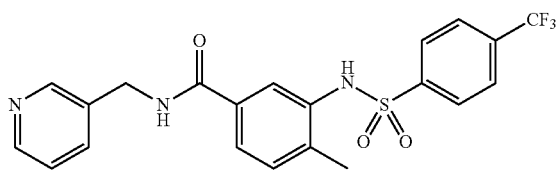 [SMILES: Cc1ccc(C(=O)NCc2cccnc2)cc1NS(=O)(=O)c1ccc(C(F)(F)F)cc1]

According to the method of step 2 in Example 1, the title compound was synthesized from 3-amino-4-methyl-N-(pyridin-3-ylmethyl) benzamide and 4-trifluoromethylbenzenesulfonyl chloride.

$^1$H NMR (400 MHz, DMSO-d$_6$) δ 10.04 (s, 1H), 9.05 (s, 1H), 8.53 (d, J=1.8 Hz, 1H), 8.46 (dd, J=4.8, 1.5 Hz, 1H), 7.96 (d, J=8.3 Hz, 2H), 7.86 (d, J=8.2 Hz, 2H), 7.72-7.64 (m, 2H), 7.61 (d, J=1.8 Hz, 1H), 7.35 (ddd, J=7.9, 4.8, 0.7 Hz, 1H), 7.26 (d, J=8.1 Hz, 1H), 4.46 (d, J=5.9 Hz, 2H), 1.96 (s, 3H).

Example 19: 4-methyl-N-(pyridin-3-ylmethyl)-3-((3-(trifluoromethyl)phenyl) sulfonamido)benzamide

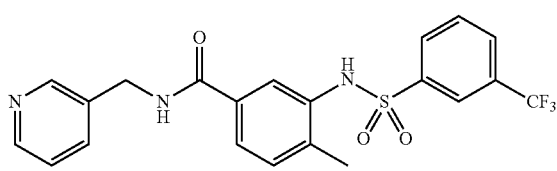 [SMILES: Cc1ccc(C(=O)NCc2cccnc2)cc1NS(=O)(=O)c1cccc(C(F)(F)F)c1]

According to the method of step 2 in Example 1, the title compound was synthesized from 3-amino-4-methyl-N-(pyridin-3-ylmethyl) benzamide and 3-trifluoromethylbenzenesulfonyl chloride.

$^1$H NMR (400 MHz, DMSO-d$_6$) δ 10.06 (s, 1H), 9.27 (t, J=5.5 Hz, 1H), 8.84 (d, J=1.4 Hz, 1H), 8.79 (d, J=5.4 Hz, 1H), 8.39 (d, J=7.8 Hz, 1H), 8.07 (d, J=7.8 Hz, 1H), 8.00-7.90 (m, 2H), 7.89-7.80 (m, 2H), 7.73 (dd, J=8.0, 1.8 Hz, 1H), 7.54 (d, J=1.7 Hz, 1H), 7.28 (d, J=8.1 Hz, 1H), 4.60 (d, J=5.8 Hz, 2H), 1.98 (s, 3H).
MS (ESI+) m/z 450.3 [M+H]+.

Example 20: 3-((4-fluorophenyl)sulfonamido)-4-methyl-N-(pyridin-3-ylmethyl)benzamide

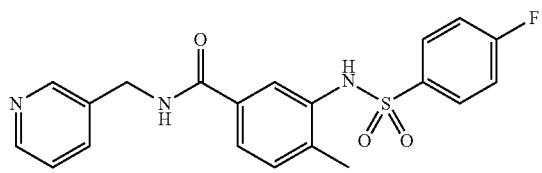 [SMILES: Cc1ccc(C(=O)NCc2cccnc2)cc1NS(=O)(=O)c1ccc(F)cc1]

According to the method of step 2 in Example 1, the title compound was synthesized from 3-amino-4-methyl-N-(pyridin-3-ylmethyl) benzamide and 4-fluorobenzenesulfonyl chloride.

$^1$H NMR (400 MHz, DMSO-d$_6$) δ 9.78 (s, 1H), 9.03 (t, J=5.9 Hz, 1H), 8.53 (s, 1H), 8.46 (d, J=3.8 Hz, 1H), 7.72-7.62 (m, 3H), 7.64 (dd, J=7.9, 1.8 Hz, 1H), 7.58 (d, J=1.8 Hz, 1H), 7.43-7.33 (m, 3H), 7.24 (d, J=8.1 Hz, 1H), 4.45 (d, J=5.9 Hz, 2H), 1.98 (s, 3H).

Example 21: 3-((4-chlorophenyl)sulfonamido)-4-methyl-N-(pyridin-3-ylmethyl)benzamide

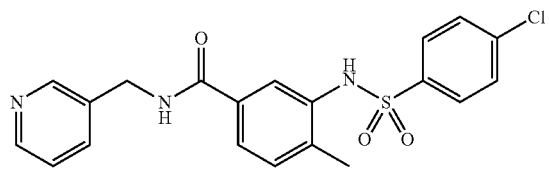 [SMILES: Cc1ccc(C(=O)NCc2cccnc2)cc1NS(=O)(=O)c1ccc(Cl)cc1]

According to the method of step 2 in Example 1, the title compound was synthesized from 3-amino-4-methyl-N-(pyridin-3-ylmethyl) benzamide and 4-chlorobenzenesulfonyl chloride.

$^1$H NMR (400 MHz, DMSO-d$_6$) δ 9.86 (s, 1H), 9.04 (t, J=5.9 Hz, 1H), 8.53 (d, J=1.9 Hz, 1H), 8.46 (dd, J=4.8, 1.6 Hz, 1H), 7.69 (dt, J=7.8, 1.9 Hz, 1H), 7.67-7.62 (m, 5H), 7.60 (d, J=1.7 Hz, 1H), 7.39-7.33 (m, 1H), 7.25 (d, J=8.0 Hz, 1H), 4.46 (d, J=5.8 Hz, 2H), 1.98 (s, 3H).

Example 22: 3-((4-isopropylphenyl)sulfonamido)-4-methyl-N-(pyridin-3-ylmethyl)benzamide

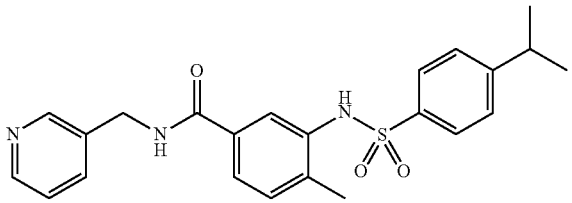 [SMILES: Cc1ccc(C(=O)NCc2cccnc2)cc1NS(=O)(=O)c1ccc(C(C)C)cc1]

According to the method of step 2 in Example 1, the title compound was synthesized from 3-amino-4-methyl-N-(pyridin-3-ylmethyl) benzamide and 4-isopropylbenzenesulfonyl chloride.

$^1$H NMR (400 MHz, DMSO-d$_6$) δ 9.63 (s, 1H), 9.02 (t, J=5.9 Hz, 1H), 8.53 (d, J=1.8 Hz, 1H), 8.46 (dd, J=4.8, 1.6 Hz, 1H), 7.69 (dt, J=7.8, 1.9 Hz, 1H), 7.65-7.59 (m, 2H), 7.56 (d, J=8.4 Hz, 2H), 7.40 (d, J=8.4 Hz, 2H), 7.38-7.33 (m, 1H), 7.21 (d, J=8.5 Hz, 1H), 4.45 (d, J=5.9 Hz, 2H), 3.01-2.88 (m, 1H), 1.94 (s, 3H), 1.18 (d, J=6.9 Hz, 6H).

Example 23: 3-((4-cyclopropylphenyl)sulfonamido)-4-methyl-N-(pyridin-3-ylmethyl)benzamide

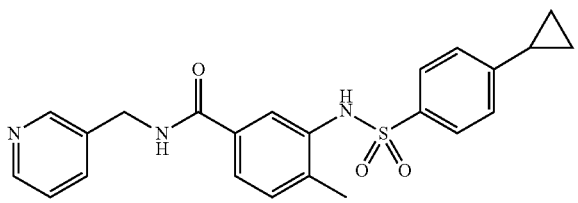 [SMILES: Cc1ccc(C(=O)NCc2cccnc2)cc1NS(=O)(=O)c1ccc(C2CC2)cc1]

According to the method of step 2 in Example 1, the title compound was synthesized from 3-amino-4-methyl-N-(pyridin-3-ylmethyl) benzamide and 4-cyclopropylbenzenesulfonyl chloride.

$^1$H NMR (400 MHz, DMSO-d$_6$) δ 9.61 (s, 1H), 9.02 (t, J=5.9 Hz, 1H), 8.53 (d, J=1.6 Hz, 1H), 8.46 (dd, J=4.7, 1.4 Hz, 1H), 7.69 (dt, J=7.9, 2.1 Hz, 1H), 7.66-7.57 (m, 2H), 7.49 (d, J=8.5 Hz, 2H), 7.39-7.33 (m, 1H), 7.23-7.18 (m, 3H), 4.45 (d, J=5.9 Hz, 2H), 2.03-1.96 (m, 1H), 1.95 (s, 3H), 1.10-0.94 (m, 2H), 0.78-0.65 (m, 2H).

Example 24: 4-methyl-3-((4-n-propylphenyl) sulfonamido)-N-(pyridin-3-ylmethyl) benzamide

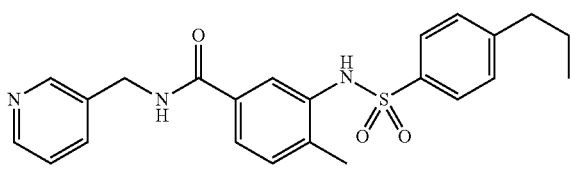 [SMILES: CCCc1ccc(S(=O)(=O)Nc2cc(C(=O)NCc3cccnc3)ccc2C)cc1]

According to the method of step 2 in Example 1, the title compound was synthesized from 3-amino-4-methyl-N-(pyridin-3-ylmethyl) benzamide and 4-n-propylbenzenesulfonyl chloride.

$^1$H NMR (400 MHz, DMSO-d$_6$) δ 9.63 (s, 1H), 9.02 (t, J=5.9 Hz, 1H), 8.53 (d, J=1.8 Hz, 1H), 8.46 (dd, J=4.8, 1.5 Hz, 1H), 7.69 (dt, J=7.7, 1.7 Hz, 1H), 7.65-7.59 (m, 2H), 7.53 (d, J=8.3 Hz, 2H), 7.39-7.31 (m, 3H), 7.21 (d, J=7.9 Hz, 1H), 4.45 (d, J=5.8 Hz, 2H), 2.60 (t, J=7.5 Hz, 2H), 1.92 (s, 3H), 1.66-1.49 (m, 2H), 0.85 (t, J=7.3 Hz, 3H).

Example 25: 3-((2,3-dihydro-1H-indene)-5-sulfonamido)-4-methyl-N-(pyridin-3-ylmethyl)benzamide

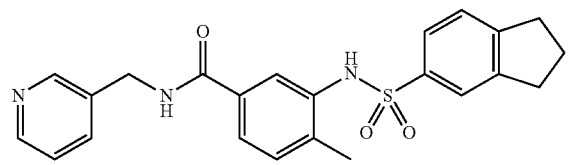 [SMILES: Cc1ccc(C(=O)NCc2cccnc2)cc1NS(=O)(=O)c1ccc2c(c1)CCC2]

According to the method of step 2 in Example 1, the title compound was synthesized from 3-amino-4-methyl-N-(pyridin-3-ylmethyl) benzamide and 2,3-dihydro-1H-indene-5-sulfonyl chloride.

$^1$H NMR (400 MHz, DMSO-d$_6$) δ 9.59 (s, 1H), 9.02 (t, J=5.9 Hz, 1H), 8.52 (d, J=1.6 Hz, 1H), 8.46 (dd, J=4.7, 1.5 Hz, 1H), 7.75-7.65 (m, 1H), 7.64-7.58 (m, 2H), 7.51-7.46 (m, 1H), 7.44-7.39 (m, 1H), 7.38-7.32 (m, 2H), 7.21 (dd, J=8.4, 0.4 Hz, 1H), 4.45 (d, J=5.9 Hz, 2H), 2.98-2.76 (m, 4H), 2.09-1.92 (m, 5H).

Example 26: 3-(benzo[d][1,3]dioxole-5-sulfonamido)-4-methyl-N-(pyridin-3-ylmethyl)benzamide

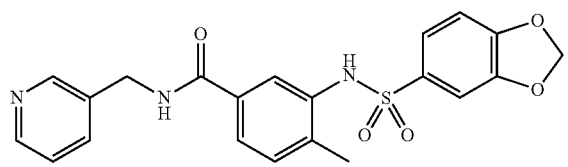 [SMILES: Cc1ccc(C(=O)NCc2cccnc2)cc1NS(=O)(=O)c1ccc2c(c1)OCO2]

According to the method of step 2 in Example 1, the title compound was synthesized from 3-amino-4-methyl-N-(pyridin-3-ylmethyl) benzamide and benzo[d][1,3]dioxole-5-sulfonyl chloride.

$^1$H NMR (400 MHz, DMSO-d$_6$) δ 9.60 (s, 1H), 9.03 (t, J=5.9 Hz, 1H), 8.53 (s, 1H), 8.46 (d, J=3.9 Hz, 1H), 7.73-7.67 (m, 1H), 7.63 (dd, J=7.8, 1.8 Hz, 1H), 7.60 (d, J=1.8 Hz, 1H), 7.39-7.32 (m, 1H), 7.24 (d, J=7.9 Hz, 1H), 7.15 (dd, J=8.2, 1.9 Hz, 1H), 7.10 (d, J=1.8 Hz, 1H), 7.02 (d, J=8.2 Hz, 1H), 6.15 (s, 2H), 4.46 (d, J=5.9 Hz, 2H), 2.03 (s, 3H).

Example 27: 3-((2,3-dihydrobenzofuran)-5-sulfonamido)-4-methyl-N-(pyridin-3-ylmethyl)benzamide

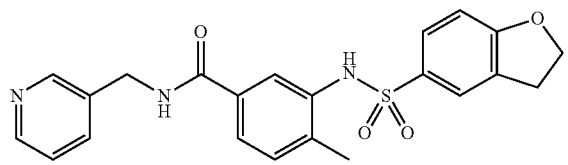 [SMILES: Cc1ccc(C(=O)NCc2cccnc2)cc1NS(=O)(=O)c1ccc2c(c1)CCO2]

According to the method of step 2 in Example 1, the title compound was synthesized from 3-amino-4-methyl-N-(pyridin-3-ylmethyl) benzamide and 2,3-dihydrobenzofuran-5-sulfonyl chloride.

$^1$H NMR (400 MHz, DMSO-d$_6$) δ 9.52 (s, 1H), 9.16 (t, J=5.1 Hz, 1H), 8.78 (s, 1H), 8.73 (d, J=4.2 Hz, 1H), 8.27 (d, J=5.3 Hz, 1H), 7.85 (s, 1H), 7.64 (dd, J=4.1, 2.3 Hz, 2H), 7.49 (d, J=1.8 Hz, 1H), 7.38 (dd, J=8.4, 2.1 Hz, 1H), 7.24 (dd, J=8.4, 0.6 Hz, 1H), 6.85 (d, J=8.4 Hz, 1H), 4.61 (t, J=8.8 Hz, 2H), 4.58 (d, J=5.6 Hz, 2H), 3.18 (dd, J=8.8 Hz, 2H), 2.01 (s, 3H).

MS (ESI+) m/z 424.3 [M+H]+.

Example 28: 3-((2,3-dihydrobenzo[b][1,4]dioxine)-6-sulfonamido)-4-methyl-N-(pyridin-3-ylmethyl) benzamide

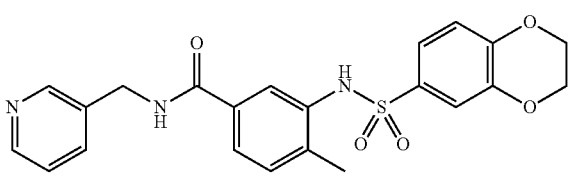 [SMILES: Cc1ccc(C(=O)NCc2cccnc2)cc1NS(=O)(=O)c1ccc2c(c1)OCCO2]

According to the method of step 2 in Example 1, the title compound was synthesized from 3-amino-4-methyl-N-(pyridin-3-ylmethyl) benzamide and (2,3-dihydrobenzo[b][1,4]dioxin)-6-sulfonyl chloride.

$^1$H NMR (400 MHz, DMSO-d$_6$) δ 9.61 (s, 1H), 9.21 (t, J=5.6 Hz, 1H), 8.83 (s, 1H), 8.77 (d, J=5.4 Hz, 1H), 8.37 (d, J=7.7 Hz, 1H), 7.95-7.86 (m, 1H), 7.66 (dd, J=7.9, 1.6 Hz, 1H), 7.63 (d, J=1.7 Hz, 1H), 7.25 (d, J=8.0 Hz, 1H), 7.11-7.06 (m, 2H), 6.98 (d, J=9.0 Hz, 1H), 4.60 (d, J=5.7 Hz, 2H), 4.38-4.23 (m, 4H), 2.01 (s, 3H).

MS (ESI+) m/z 440.3 [M+H]+.

Example 29: 4-methyl-3-(naphthalene-2-sulfonamido)-N-(pyridin-3-ylmethyl)benzamide

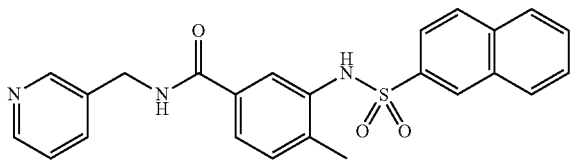 [SMILES: Cc1ccc(C(=O)NCc2cccnc2)cc1NS(=O)(=O)c1ccc2ccccc2c1]

According to the method of step 2 in Example 1, the title compound was synthesized from 3-amino-4-methyl-N-(pyridin-3-ylmethyl) benzamide and naphthalene-2-sulfonyl chloride.

$^1$H NMR (400 MHz, DMSO-d$_6$) δ 9.85 (s, 1H), 9.01 (t, J=5.9 Hz, 1H), 8.51 (d, J=1.6 Hz, 1H), 8.46 (dd, J=4.7, 1.4 Hz, 1H), 8.28 (d, J=1.6 Hz, 1H), 8.13-8.00 (m, 3H), 7.77-7.58 (m, 6H), 7.36-7.31 (m, 1H), 7.18 (d, J=8.1 Hz, 1H), 4.43 (d, J=5.8 Hz, 2H), 1.94 (s, 3H).

Example 30: 4-methyl-3-(5-methylthiophene)-2-sulfonamido)-N-(pyridin-3-ylmethyl)benzamide

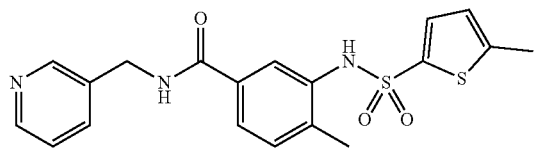 [SMILES: Cc1ccc(S(=O)(=O)Nc2cc(C(=O)NCc3cccnc3)ccc2C)s1]

According to the method of step 2 in Example 1, the title compound was synthesized from 3-amino-4-methyl-N-(pyridin-3-ylmethyl) benzamide and 5-methylthiophene-2-sulfonyl chloride.

$^1$H NMR (400 MHz, DMSO-d$_6$) δ 9.87 (s, 1H), 9.21 (t, J=5.7 Hz, 1H), 8.81 (d, J=1.4 Hz, 1H), 8.76 (d, J=5.4 Hz, 1H), 8.34 (d, J=8.0 Hz, 1H), 7.90 (dd, J=7.9, 5.5 Hz, 1H), 7.73-7.67 (m, 2H), 7.31-7.25 (m, 1H), 7.19 (d, J=3.7 Hz, 1H), 6.84 (dd, J=3.7, 1.1 Hz, 1H), 4.60 (d, J=5.7 Hz, 2H), 2.46 (s, 3H), 2.03 (s, 3H).

MS (ESI+) m/z 402.3 [M+H]+.

Example 31: 3-((5-chlorothiophene)-2-sulfonamido)-4-methyl-N-(pyridin-3-ylmethyl)benzamide

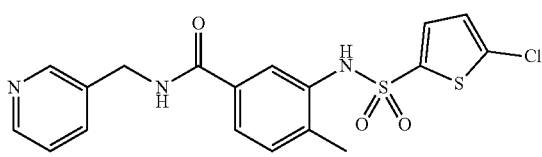 [SMILES: Cc1ccc(C(=O)NCc2cccnc2)cc1NS(=O)(=O)c1ccc(Cl)s1]

According to the method of step 2 in Example 1, the title compound was synthesized from 3-amino-4-methyl-N-(pyridin-3-ylmethyl) benzamide and 5-chlorothiophene-2-sulfonyl chloride.

$^1$H NMR (400 MHz, DMSO-d$_6$) δ 10.13 (s, 1H), 9.08 (t, J=5.8 Hz, 1H), 8.54 (s, 1H), 8.47 (d, J=3.1 Hz, 1H), 7.73-7.67 (m, 2H), 7.64 (d, J=1.8 Hz, 1H), 7.36 (dd, J=7.8, 4.7 Hz, 1H), 7.31 (d, J=8.0 Hz, 1H), 7.29 (d, J=4.1 Hz, 1H), 7.23 (d, J=4.1 Hz, 1H), 4.47 (d, J=5.9 Hz, 2H), 2.08 (s, 3H).

Example 32: 3-((6-methoxypyridine)-3-sulfonamido)-4-methyl-N-(pyridin-3-ylmethyl)benzamide

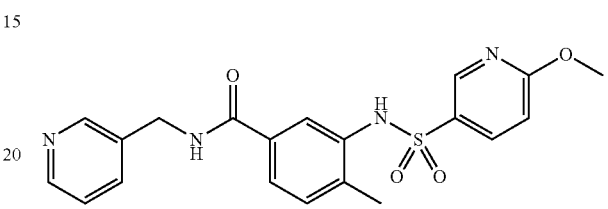

According to the method of step 2 in Example 1, the title compound was synthesized from 3-amino-4-methyl-N-(pyridin-3-ylmethyl) benzamide and 6-methoxypyridine-3-sulfonyl chloride.

$^1$H NMR (400 MHz, DMSO-d$_6$) δ 9.87 (s, 1H), 9.22 (t, J=5.5 Hz, 1H), 8.82 (s, 1H), 8.76 (d, J=4.0 Hz, 1H), 8.43-8.32 (m, 2H), 8.00-7.83 (m, 2H), 7.70 (d, J=7.9 Hz, 1H), 7.61 (d, J=1.7 Hz, 1H), 7.28 (d, J=8.1 Hz, 1H), 6.99 (dd, J=8.8, 0.4 Hz, 1H), 4.59 (d, J=5.7 Hz, 2H), 3.90 (s, 3H), 2.04 (s, 3H).

MS (ESI+) m/z 413.3 [M+H]+.

Example 33: 4-methyl-3-((4-methylphenyl)sulfonamido)-N-((6-methylpyridin-3-yl)methyl)benzamide

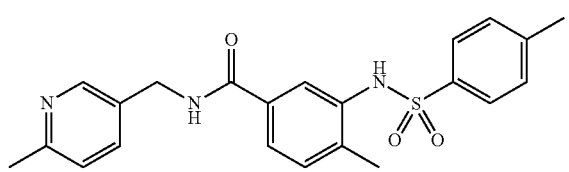

Step 1: Preparation of methyl 4-methyl-3-((4-methylphenyl)sulfonamido) benzoate

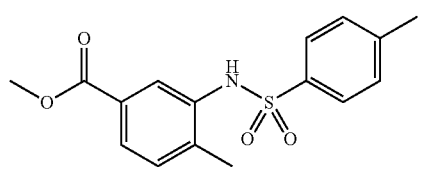

A mixture of 3-amino-4-methyl benzoic acid (1.65 g, 10 mmol), p-toluenesulfonyl chloride (2.8 g, 12 mmol), pyridine (1.19 g, 15 mmol) and DMAP(0.122 g, 1 mmol) in DCM(40 mL) was stirred at rt overnight. The reaction mixture was diluted with water (100 mL) and acidified to pH=3-4 with dilute hydrochloric acid. The mixture was extracted with dichloromethane (50 mL×3). The combined organic layers were washed with water (100 mL×2) and saline (100 mL), dried with anhydrous sodium sulfate, filtered and concentrated. The residue was purified by column chromatography (silica gel, PE/EtOAc=3:1) to obtain the product as yellow oil (2.82 g, yield 88%).

¹H NMR (400 MHz, DMSO-d₆) δ 9.73 (s, 1H), 7.70-7.63 (m, 2H), 7.55 (d, J=8.0H, 2H), 7.36 (d, J=8.0 Hz, 2H), 7.28 (d, J=7.7 Hz, 1H), 3.81 (s, 3H), 2.36 (s, 3H), 2.03 (s, 3H).
MS (ESI+) m/z 319.8 [M+H]+.

Step 2: Preparation of 4-methyl-3-((4-methylphenyl)sulfonamido)benzoic Acid

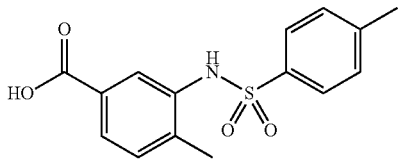 [SMILES: Cc1ccc(S(=O)(=O)Nc2cc(C(=O)O)ccc2C)cc1]

The mixture of methyl 4-methyl-3-((4-methylphenyl) sulfonamido) benzoate (2.71 g, 8.5 mmol) and sodium hydroxide (1.36 g, 34 mmol, 4 eq.) in methanol (51 mL) and water (17 mL) was refluxed for 7 hours. The resulting mixture was evaporated to dryness under reduced pressure, and the reaction mixture was diluted with water (100 mL), acidified to pH=2 with concentrated hydrochloric acid, and extracted with ethyl acetate (50 mL×3). The combined organic layers were washed with water (100 mL×2) and saline (100 mL), dried with anhydrous sodium sulfate, filtered, and concentrated until solid began to precipitate in the solution. The resulting suspension was left still for 1 hour, and the solid was collected by suction filtration and dried to afford a light yellow solid (2.1 g, yield 81%).

¹H NMR (400 MHz, DMSO-d₆) δ 12.89 (br s, 1H), 9.69 (br s, 1H), 7.66 (dd, J=7.8, 1.6 Hz, 1H), 7.63 (d, J=1.5 Hz, 1H), 7.55 (d, J=8.2 Hz, 2H), 7.36 (d, J=8.1 Hz, 2H), 7.25 (d, J=7.9 Hz, 1H), 2.36 (s, 3H), 2.05 (s, 3H).
MS (ESI+) m/z 305.8 [M+H]+.

Step 3: Preparation of 4-methyl-3-((4-methylphenyl)sulfonamido)-N-((6-methylpyridin-3-yl)methyl)benzamide

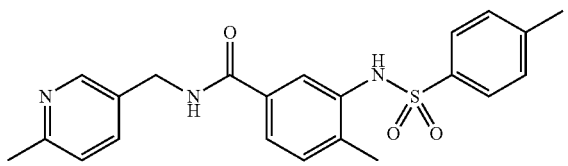

The reaction mixture of 4-methyl-3-((4-methylphenyl) sulfonamido) benzoic acid (0.153 g, 0.5 mmol), 6-methylpyridin-3-ylmethylamine (0.080 g, 0.65 mmol), HATU (0.285 g, 0.75 mmol) and triethylamine (0.152 g, 1.5 mmol) in DCM(10 mL) was stirred overnight. Water (50 mL) was added, and the resulting mixture was extracted with DCM (30 mL×3). The combined organic layers were washed with water (30 mL×2) and saline (30 mL), dried with anhydrous sodium sulfate, filtered and concentrated. The residue was purified by preparative thin layer chromatography (silica gel, DCM/MeOH=15:1) to obtain a yellow foamy is solid (126 mg, yield 62%).

¹H NMR (400 MHz, DMSO-d₆) δ 9.63 (s, 1H), 8.97 (t, J=5.9 Hz, 1H), 8.38 (d, J=2.1 Hz, 1H), 7.64-7.55 (m, 3H), 7.55-7.49 (m, 2H), 7.33 (d, J=8.0 Hz, 2H), 7.20 (d, J=7.8 Hz, 2H), 4.40 (d, J=5.8 Hz, 2H), 2.44 (s, 3H), 2.35 (s, 3H), 1.95 (s, 3H).

Example 34: N-((6-methoxypyridin-3-yl)methyl)-4-methyl-3-((4-methylphenyl) sulfonamido)benzamide

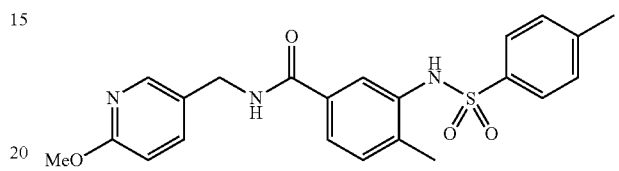

The title compound was synthesized from 4-methyl-3-((4-methylphenyl) sulfonamido) benzoic acid and 6-methoxypyridin-3-ylmethylamine according to the method of Example 33.

¹H NMR (400 MHz, DMSO-d₆) δ 9.63 (s, 1H), 8.93 (t, J=5.9 Hz, 1H), 8.10 (d, J=2.1 Hz, 1H), 7.69-7.56 (m, 3H), 7.52 (d, J=8.3 Hz, 2H), 7.33 (d, J=8.0 Hz, 2H), 7.20 (d, J=8.0 Hz, 1H), 6.79 (dd, J=8.8, 0.4 Hz, 1H), 4.36 (d, J=5.8 Hz, 2H), 3.83 (s, 3H), 2.35 (s, 3H), 1.94 (s, 3H).

Example 35: 4-methyl-3-((4-methylphenyl) sulfonamido)-N-((6-(trifluoromethyl) pyridin-3-yl)methyl) benzamide

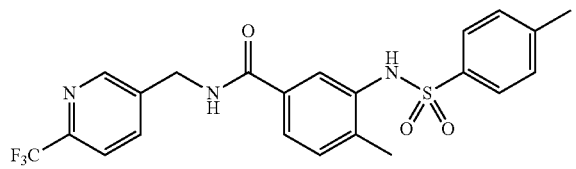 [SMILES: Cc1ccc(S(=O)(=O)Nc2cc(C(=O)NCc3ccc(C(F)(F)F)nc3)ccc2C)cc1]

According to the method of Example 34, the title compound was synthesized from 4-methyl-3-((4-methylphenyl) sulfonamido) benzoic acid and 6-trifluoromethylpyridin-3-ylmethylamine.

¹H NMR (400 MHz, DMSO-d₆) δ 9.65 (s, 1H), 9.11 (t, J=5.8 Hz, 1H), 8.71 (d, J=1.4 Hz, 1H), 7.97 (dd, J=8.1, 1.5 Hz, 1H), 7.88 (d, J=8.1 Hz, 1H), 7.67-7.58 (m, 2H), 7.52 (d, J=8.3 Hz, 2H), 7.33 (d, J=8.1 Hz, 2H), 7.22 (d, J=8.6 Hz, 1H), 4.55 (d, J=5.8 Hz, 2H), 2.35 (s, 3H), 1.96 (s, 3H).

Evaluation of Pharmacological Activity

Experimental Example 1: MTT Assay was Used to Determine the Survival Rate of Tumor Cells DU145 cells (human prostate cancer cells) in logarithmic growth phase were digested with 0.25% trypsin-EDTA to prepare single cell suspension, which was inoculated into 96-well plate overnight according to 1500 cells/well/100 μL, and fresh medium containing different concentrations of compounds to be tested and corresponding solvent control was added, and 100 μL(DMSO final concentration <0.1%)

was added to each well, and the 96-well plate was further cultured at 37° C. for 72 h. 20 μL of freshly prepared PBS solution containing 5 mg/mL MTT was added to each well, and the 96-well plate was further cultured for 4 h. After the supernatant was discarded, 180 μL of DMSO was added to each well to dissolve the MTT formazan precipitate. After the 96-well plate was shaked and mixed by a micro oscillator, the optical density (OD) at the detection wavelength of 570 nm was measured. With DMSO-treated tumor cells as the control group, the inhibition rate on the growth of tumor cells of the compound to be tested was calculated from the following formula, and the $IC_{50}$ was calculated according to the median-effect equation.

Inhibition rate (%)=(average OD value of control group-average OD value of dosing group)/average OD value of control group×100%

The results are shown in table 1. The experimental results showed that all the examples showed antiproliferative activity against human prostate cancer DU145, and their $IC_{50}$ values were all less than 10 μM.

TABLE 1

Antiproliferative activity against human prostate cancer cell DU145

| Example | $IC_{50}$ (μM) |
|---|---|
| 1 | 0.12 ± 0.03 |
| 2 | 0.7 ± 0.15 |
| 3 | 0.79 ± 0.13 |
| 4 | 0.8 ± 0.12 |
| 6 | 0.86 ± 0.08 |
| 7 | 0.34 ± 0.01 |
| 9 | 0.9 ± 0.02 |
| 10 | 0.34 ± 0.01 |
| 11 | 2.0 ± 0.03 |
| 12 | 0.04 ± 0.01 |
| 13 | 0.18 ± 0.08 |
| 14 | 2.5 ± 0.02 |
| 15 | 0.86 ± 0.06 |
| 16 | 0.97 ± 0.03 |
| 17 | 0.5 ± 0.04 |
| 20 | 3.47 ± 1.22 |
| 21 | 0.93 ± 0.05 |
| 22 | 1 ± 0.16 |
| 23 | 0.05 ± 0.008 |
| 25 | 0.9 ± 0.04 |
| 26 | 0.61 ± 0.14 |
| 27 | 1.2 ± 0.01 |
| 28 | 0.42 ± 0.01 |
| 29 | 1 ± 0.07 |
| 30 | 1.2 ± 0.03 |
| 32 | 0.4 ± 0.02 |
| 33 | 0.008 ± 0.001 |
| 34 | 0.006 ± 0.002 |
| 35 | 0.2 ± 0.07 |

Experimental Example 2: Luciferase Double Reporter Gene Experiment

The luciferase plasmids STAT3-TA-Luc and pGMLR-TK were transiently co-transfected into DU145 cells by Lipofectamine 3000. After staying overnight, different concentrations of compounds to be tested were added and cultured for 24 hours. The supernatant was discarded, and the residue was washed twice with PBS, and then 20 μL of lysis solution was added to shake and lyse for 5 min. The supernatant was transferred to a 96-well Costar whiteplate, and 70 μL of Dual-Glo luciferase substrate solution was added, and the relative fluorescence intensity of firefly luciferase was detected, and then 70 μL of Stop-Glo substrate solution was added, and the relative fluorescence intensity of sea kidney luciferase was detected, the normalized value was obtained, and the inhibition rate and $IC_{50}$ value were calculated.

The results are shown in table 2. The experimental results showed that Examples 1, 6, 9, 12, 13, 17, 20, 23, 30, 33, 34 and 35 showed obvious STAT3 transcription inhibition activity in the STAT3 specific luciferase double reporter gene experiment of human prostate cancer cell DU145.

TABLE 2

Experimental results of luciferase double reporter gene on human prostate cancer cell DU145 with high STAT3 expression

| Example | $IC_{50}$ (μM) |
|---|---|
| 1 | 7 ± 1.3 |
| 6 | 9.7 ± 1.3 |
| 9 | 6.2 ± 0.3 |
| 12 | 1 ± 0.35 |
| 13 | 10 ± 2.1 |
| 17 | 8.2 ± 0.02 |
| 20 | 15 ± 1.4 |
| 23 | 1 ± 0.19 |
| 30 | 17.5 ± 0.3 |
| 33 | 0.5 ± 0.12 |
| 34 | 0.8 ± 0.27 |
| 35 | 8 ± 0.43 |

Experimental Example 3: The Expression of p-STAT3 was Detected by Western Blotting DU145 cells treated for 16 h with different concentrations of examples 12, 23, 33 and 34 and DU145 cells in control group were collected and washed twice with pre-cooled PBS. After appropriate amount of RIPA lysate (50 mM Tris-HCl, 1 mM EDTA, 1% Triton X-100, 150 mM NaCl, 0.1% SDS, 1 mM NaF, $Na_3VO_4$, protease inhibitor, pH 7.4) was added to lyse for 1 h on ice, the reaction mixture was centrifuged at 4° C., 12,000 rpm for 20 min, and then the supernatant was collected for protein quantification and boiled for denaturation. Equal amount of protein was taken for 10% SDS-PAGE electrophoresis. The specific antibodies of p-STAT3(Tyr705) and STAT3 were used as primary antibody, which was incubated overnight at 4° C. The corresponding HRP-labeled secondary antibody was used, incubated at room temperature for 2 h, and washed. ECL chemiluminescence substrate reaction solution was added to develop in gel imaging system, and the image was saved. β-actin was used as internal reference.

The results are shown in FIG. 1.

Experimental Example 4: Study on the Efficacy of Xenotransplantation in Nude Mice Tumor cells of human prostate cancer DU145 were collected under aseptic conditions, and the cell density was adjusted to $1×10^6$ cells/mL with sterilized normal saline, and then 0.2 mL of which was inoculated subcutaneously in the axillary back of nude mice. When the tumor grew to 1 cm in diameter, it was taken out under aseptic conditions, cut into tumor blocks with the size of 1 mm×1 mm, and inoculated subcutaneously in the axillary back of nude mice. Two weeks later, after the tumor grew to 100-300 $mm^3$, the animals were randomly divided into groups and began to be administered (recorded as day 0). The compound to be tested is administered orally. The animals were weighed twice a week and the length and width of tumor were measured with vernier caliper. After the experiment, the nude mice were dislocated and killed, and the tumor tissues were stripped, weighed and photographed. Finally, the tumor inhibition rate was calculated, and the anti-tumor effect was evaluated by the tumor inhibition rate. The results are shown in tables 3 and 4 and FIGS. 2 and 3.

The tumor volume is calculated according to the following formula:

Tumor volume=$(a \times b^2)/2$, where a and b represent the length and width of tumor respectively.

The tumor growth inhibition percentage is calculated according to the following formula: tumor growth inhibition (%)=$(1-T/C) \times 100$, T is the tumor volume of group of the compound to be tested, and C is the tumor volume of the solvent control group.

Figure 2:
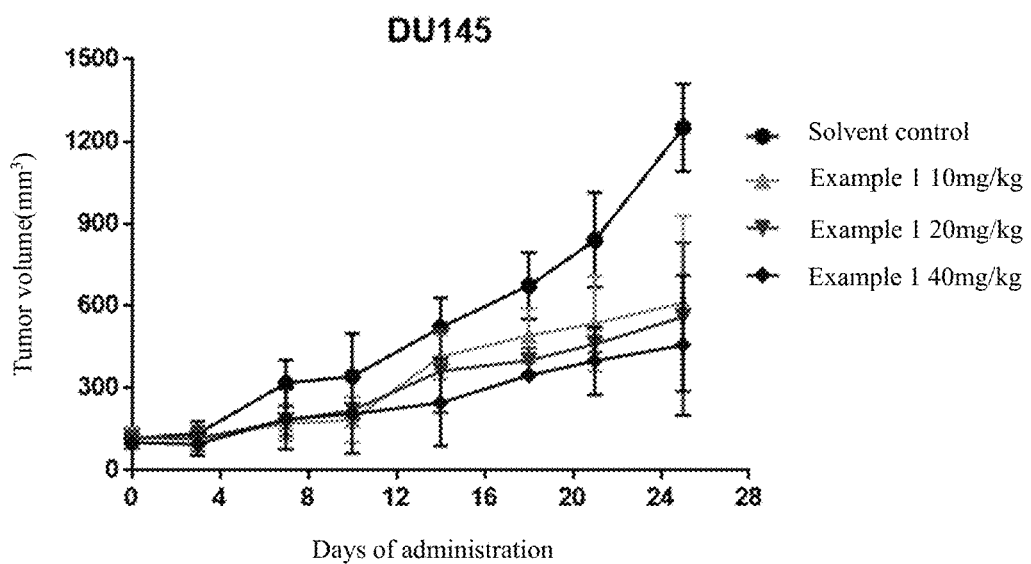
FIG. 2 is a tumor growth curve, which shows the inhibitory effect of Example 1 on the growth of xenograft tumor formed by subcutaneous xenotransplantation of human prostate cancer DU145 in nude mice.
Figure 3:
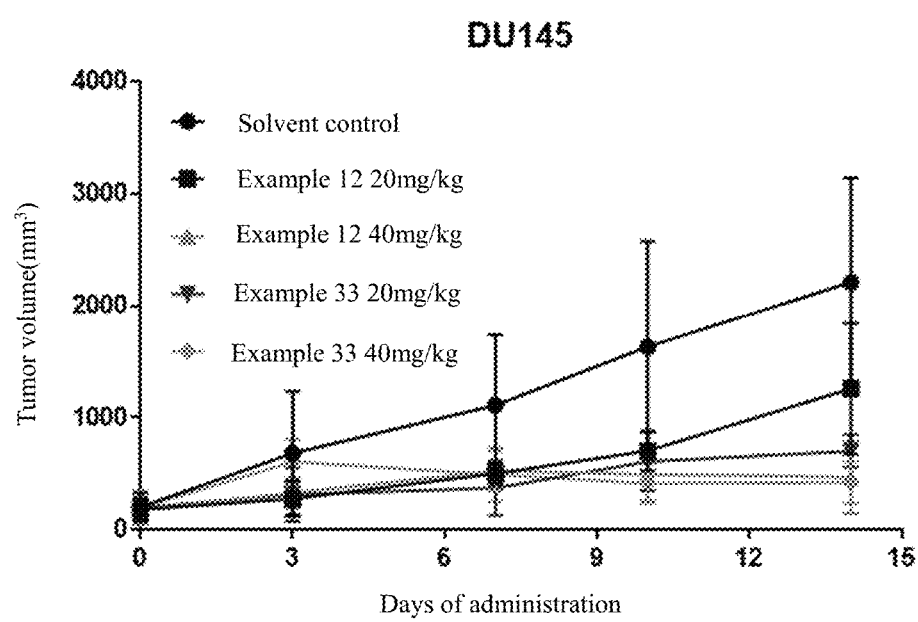
FIG. 3 is a tumor growth curve, which shows the inhibitory effect of Examples 12 and 33 on the growth of xenograft tumor formed by subcutaneous xenotransplantation of human prostate cancer DU145 in nude mice.

The results are shown in tables 3 and 4, and FIGS. 2 and 3.

TABLE 3

The inhibitory effect of Example 1 on the growth of xenograft tumor formed by subcutaneous xenotransplantation of human prostate cancer DU145 in nude mice

| Example | Dose (mg/kg × times) | Tumor growth inhibition (%) |
|---|---|---|
| 1 | 10 × 7 | 58.8*** |
|   | 20 × 7 | 62.7*** |
|   | 40 × 7 | 73.5*** |

***p < 0.001

TABLE 4

The inhibitory effect of Examples 12 and 33 on the growth of xenograft tumor formed by subcutaneous xenotransplantation of human prostate cancer DU 145 in nude mice

| Example | Dose (mg/kg × times) | Tumor growth inhibition (%) |
|---|---|---|
| 12 | 20 × 14 | 40.4 |
|    | 40 × 11 | 79.7*** |
| 33 | 20 × 6  | 63.0** |
|    | 40 × 5  | 80.0** |

***p < 0.001;
**p < 0.01

Summary of Pharmacological Activities:

All the examples showed antiproliferative activity against human prostate cancer DU145, and their $IC_{50}$ values were all less than 10 μM m. Examples 1, 6, 9, 12, 13, 17, 20, 23, 30, 33, 34 and 35 showed obvious STAT3 transcription inhibition activity in the STAT3 specific luciferase double reporter gene experiment of human prostate cancer cell DU145.

Example 1 showed obvious inhibitory activity on STAT3 phosphorylation of human prostate cancer DU145 at 1 μM concentration, Examples 12 and 23 showed obvious inhibitory activity on STAT3 phosphorylation of human prostate cancer DU145 at 0.5 μM concentration, and Examples 33 and 34 showed obvious inhibitory activity on STAT3 phosphorylation of human prostate cancer DU145 at 0.1 μM concentration. Among them, Examples 1, 12 and 33 have significant inhibitory effects on the growth of xenograft tumor formed by subcutaneous xenotransplantation of human prostate cancer DU145 in nude mice.

The invention claimed is:

1. A compound represented by Formula (I), or a stereoisomer, a geometric isomer, a tautomer or a pharmaceutically acceptable salt thereof:

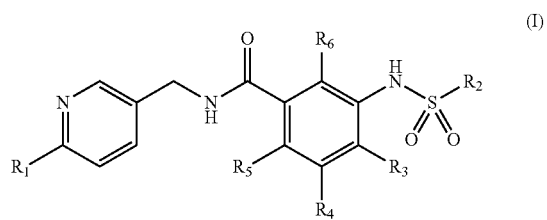

wherein, $R_1$ is selected from hydrogen, cyano, difluoromethyl, trifluoromethyl, halogen, $C_{1-3}$ alkyl, $C_{1-3}$ alkoxy;

$R_2$ is selected from:

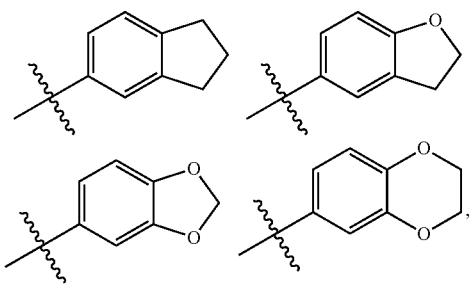

$R_3$, $R_4$, $R_5$, $R_6$ are each independently selected from hydrogen, cyano, difluoromethyl, trifluoromethyl, halogen, $C_{1-3}$ alkyl, $C_{1-3}$ alkoxy.

2. The compound according to claim 1, or a stereoisomer, a geometric isomer, a tautomer or a pharmaceutically acceptable salt thereof, characterized in that,
$R_1$ is selected from hydrogen, cyano, difluoromethyl, trifluoromethyl, chlorine, methyl, ethyl, n-propyl, isopropyl, methoxy or ethoxy.

3. The compound according to claim 1, or a stereoisomer, a geometric isomer, a tautomer or a pharmaceutically acceptable salt thereof, characterized in that, $R_3$, $R_4$, $R_5$, $R_6$ are each independently selected from hydrogen, cyano, difluoromethyl, trifluoromethyl, fluorine, chlorine, methyl, ethyl, methoxy.

4. The compound according to claim 3, or a stereoisomer, a geometric isomer, a tautomer or a pharmaceutically acceptable salt thereof, characterized in that, $R_3$ is selected from methyl, $R_4$, $R_5$ and $R_6$ are selected from hydrogen.

5. A pharmaceutical composition comprising at least one compound according to claim 1, or a stereoisomer, a geometric isomer, a tautomer or a pharmaceutically acceptable salt thereof and optionally a pharmaceutically acceptable carrier and/or excipient.

6. The pharmaceutical composition according to claim 5, characterized in that, the pharmaceutical composition further comprises other active pharmaceutical ingredient in addition to the compound, or a stereoisomer, a geometric isomer, a tautomer or a pharmaceutically acceptable salt thereof.

7. A method for treating STAT3-mediated diseases in a subject, comprising administering the compound according to claim 1, or a stereoisomer, a geometric isomer, a tautomer or a pharmaceutically acceptable salt thereof to the subject in need thereof.

8. Method according to claim 7, characterized in that, the STAT3-mediated diseases include tumors, autoimmune diseases, renal diseases, cardiovascular diseases, inflammation, metabolic/endocrine dysfunction or neurological diseases.

9. The compound according to claim 2, or a stereoisomer, a geometric isomer, a tautomer or a pharmaceutically acceptable salt thereof, characterized in that, $R_3$, $R_4$, $R_5$, $R_6$ are each independently selected from hydrogen, cyano, difluoromethyl, trifluoromethyl, fluorine, chlorine, methyl, ethyl, methoxy.

10. The compound according to claim 9, or a stereoisomer, a geometric isomer, a tautomer or a pharmaceutically acceptable salt thereof, characterized in that, $R_3$ is selected from methyl, $R_4$, $R_5$ and $R_6$ are selected from hydrogen.

* * * * *